(12) United States Patent
Yawata et al.

(10) Patent No.: US 7,884,146 B2
(45) Date of Patent: Feb. 8, 2011

(54) POLYMER MATERIAL CONTAINING ULTRAVIOLET ABSORBENT

(75) Inventors: Toshihiko Yawata, Minami-ashigara (JP); Naoyuki Hanaki, Minami-ashigara (JP); Hisashi Mikoshiba, Haibara-gun (JP); Akihiro Kaneko, Ashigarakami-gun (JP)

(73) Assignee: Fujifilm Corporation, Minato-Ku, Tokyo (JP)

( * ) Notice: Subject to any disclaimer, the term of this patent is extended or adjusted under 35 U.S.C. 154(b) by 0 days.

(21) Appl. No.: 12/525,590

(22) PCT Filed: Feb. 20, 2008

(86) PCT No.: PCT/JP2008/052895

§ 371 (c)(1),
(2), (4) Date: Aug. 3, 2009

(87) PCT Pub. No.: WO2008/102822

PCT Pub. Date: Aug. 28, 2008

(65) Prior Publication Data

US 2010/0076124 A1    Mar. 25, 2010

(30) Foreign Application Priority Data

| Feb. 20, 2007 | (JP) | 2007-040064 |
| Aug. 20, 2007 | (JP) | 2007-213979 |
| Sep. 28, 2007 | (JP) | 2007-255590 |

(51) Int. Cl.
*C08K 5/45* (2006.01)
*C07D 339/06* (2006.01)

(52) U.S. Cl. .......................... 524/84; 549/32

(58) Field of Classification Search .............. 524/84; 549/32
See application file for complete search history.

(56) References Cited

U.S. PATENT DOCUMENTS

| 3,694,211 | A | 9/1972 | Sato et al. |
| 7,241,555 | B2 | 7/2007 | Watanabe et al. |
| 2004/0029040 | A1* | 2/2004 | Watanabe et al. ...... 430/270.17 |
| 2009/0153782 | A1 | 6/2009 | Fukagawa et al. |

FOREIGN PATENT DOCUMENTS

| DE | 220 028 A1 | 3/1985 |
| JP | 49-011155 B1 | 3/1974 |
| JP | 60-170842 A | 9/1985 |
| JP | 3-164722 | 7/1991 |
| JP | 5-339033 A | 12/1993 |
| JP | 5-345639 A | 12/1993 |
| JP | 6-056466 A | 3/1994 |
| JP | 6-145387 A | 5/1994 |
| JP | 7-285927 A | 10/1995 |
| JP | 2003-177235 A | 6/2003 |
| JP | 2004-066585 A | 3/2004 |
| JP | 2004-250624 | 9/2004 |
| JP | 2005-517787 A | 6/2005 |
| JP | 2007-017958 A | 1/2007 |
| JP | 2007-304287 A | 11/2007 |
| WO | WO 03/070819 A1 | 8/2003 |
| WO | WO 2007/091716 A1 | 8/2007 |

OTHER PUBLICATIONS

Form PCT/ISA/210 (International Search Report) dated May 20, 2008.
Extended European Search Report issued in corresponding European Patent Application No. 08 72 0776 dated Mar. 18, 2010.

* cited by examiner

*Primary Examiner*—Kriellion A Sanders
(74) *Attorney, Agent, or Firm*—Buchanan Ingersoll & Rooney PC

(57) ABSTRACT

A polymer material, containing at least one kind of polymer substance selected from the group consisting of acrylic acid-based polymers, polyester-based polymers, and polycarbonate-based polymers; and a compound represented by formula (2) contained in the polymer substance:

Formula (2)

$$\text{(B)}\begin{array}{c} A_{21} \\ \diagdown \\ A_{22} \end{array}\!\!=\!\!\begin{array}{c} Y_{21} \\ \diagup \\ Y_{22} \end{array}$$

wherein $A_{21}$ and $A_{22}$ each independently represent an atom other than hydrogen atom and carbon atom; $Y_{21}$ and $Y_{22}$ each independently represent a hydrogen atom or a monovalent substituent; at least one of $Y_{21}$ and $Y_{22}$ represents a substituent having a Hammett substituent constant σp of 0.2 or more; $Y_{21}$ and $Y_{22}$ may bind to each other to form a ring; and (B) represents a group of atoms necessary for forming a five- or six-membered ring with $A_{21}$, $A_{22}$ and the carbon atom.

18 Claims, No Drawings

POLYMER MATERIAL CONTAINING ULTRAVIOLET ABSORBENT

TECHNICAL FIELD

The present invention relates to a polymer material containing an ultraviolet absorbent.

BACKGROUND ART

Ultraviolet absorbents have been used in combination with various resins for providing the resins with ultraviolet-absorptivity. Both inorganic and organic ultraviolet absorbents are used. The inorganic ultraviolet absorbents (see, for example, JP-A-5-339033 ("JP-A" means unexamined published Japanese patent application), JP-A-5-345639 and JP-A-6-56466) are superior in durability properties such as weather resistance and heat resistance. However, the freedom in selecting the compound is limited, because the absorption wavelength is determined by the band gap of the compound. In addition, there is no inorganic absorbent that absorbs the light in a long-wavelength ultraviolet (UV-A) range of 320 to 400 nm. And any such absorbent that absorbs long-wavelength ultraviolet would have color because it would have absorption also in the visible range.

In contrast, the freedom in designing the absorbent structure is much wider for organic ultraviolet absorbents, and thus, it is possible to obtain absorbents having various absorption wavelengths by designing the absorbent chemical structure properly.

Various organic ultraviolet absorbent systems have been studied, and for absorption in the long-wavelength ultraviolet range, it is conceivable either to use an absorbent having the wavelength of maximal absorption in the long-wavelength ultraviolet range or to use a high concentration of absorbent. However, the absorbents described in, for example, JP-A-6-145387 and JP-A-2003-177235 having the wavelength of maximal absorption in the long-wavelength ultraviolet range are inferior in light stability, and their absorption capacity declines over time.

In contrast, benzophenone- and benzotriazole-based ultraviolet absorbents are relatively superior in light stability, and increase in concentration or film thickness leads to relatively clean blocking of the light in the longer-wavelength range (see, for example, JP-T-2005-517787 ("JP-T" means published Japanese translation of PCT application) and JP-A-7-285927). However, when such an ultraviolet absorbent is applied as mixed with a resin or the like, the film thickness is limited to several tens of μm at the most. For utilizing the film thickness to block the light in the longer-wavelength range, it is necessary to add the ultraviolet absorbent to a considerably high concentration. In such a case, there were problems of precipitation of the ultraviolet absorbent and bleed-out during long-term use. In addition, among benzophenone-based and benzotriazole-based ultraviolet absorbents, there are some ultraviolet absorbents that may cause concern about skin irritation and accumulation in body. JP-A-2007-304287, JP-A-60-170842 and JP-B-49-11155 ("JP-B" means examined Japanese patent publication) describe a five-membered ring compound containing two sulfur atoms.

DISCLOSURE OF INVENTION

According to the present invention, it is possible to provide a polymer material that is superior in productivity when kneaded with a polymer or dissolved in a solvent, resistant to precipitation of the ultraviolet absorbent and bleeding out during long-term use, superior in long-wavelength ultraviolet absorption capacity, and superior in lightfastness while keeping the absorption capacity for an extended period of time.

The inventors have found that it was possible, by using a compound having a particular structure higher in light fastness as a polymer material, to give a polymer material resistant to precipitation of the compound or bleeding out during long-term use, superior in long-wavelength ultraviolet absorption capacity, and superior in lightfastness while keeping the absorption capacity for an extended period of time. The present invention was made based on these findings.

The present invention provides the following means:

<1> A polymer material, comprising:

at least one kind of polymer substance selected from the group consisting of acrylic acid-based polymers, polyester-based polymers, and polycarbonate-based polymers; and a compound represented by formula (2) contained in the polymer substance:

Formula (2)

wherein $A_{21}$ and $A_{22}$ each independently represent an atom other than hydrogen atom and carbon atom; $Y_{21}$ and $Y_{22}$ each independently represent a hydrogen atom or a monovalent substituent; at least one of $Y_{21}$ and $Y_{22}$ represents a substituent having a Hammett substituent constant σp of 0.2 or more; $Y_{21}$ and $Y_{22}$ may bind to each other to form a ring; and (B) represents a group of atoms necessary for forming a five- or six-membered ring with $A_{21}$, $A_{22}$ and the carbon atom.

<2> The polymer material described in the above item <1>, wherein a glass transition point (Tg) of the polymer substance is −80° C. or higher and 200° C. or lower.

<3> The polymer material described in the above item <1> or <2>, wherein the polymer substance is a polyacrylate, a polycarbonate or a polyethylene terephthalate.

<4> The polymer material described in any one of the above items <1> to <3>, wherein the polymer substance is the polyethylene terephthalate; and wherein the ultraviolet absorbent is contained in an amount of 0.1 mass % to 50 mass % with respect to 100 mass % of the polyethylene terephthalate.

<5> The polymer material described in the above item <4>, wherein the polymer material is a polymer material prepared by melt-kneading of the polyethylene terephthalate and the ultraviolet absorbent at a temperature of 200° C. or higher.

<6> The polymer material described in any one of the above items <1> to <3>, wherein the polymer substance is the polyacrylate or the polycarbonate; and wherein the ultraviolet absorbent is contained in an amount of 0.1 mass % to 50 mass % with respect to 100 mass % of the polyacrylate or polycarbonate.

<7> The polymer material described in the above item <6>, wherein the polymer material is a polymer material prepared by dissolving the polyacrylate and the ultraviolet absorbent in a solvent having a boiling point of 200° C. or lower to give a solution, and applying the solution on a base plate.

<8> The polymer material described in any one of the above items <1> to <7>, wherein the compound represented by formula (2) is a compound represented by formula (3):

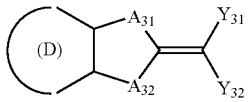

Formula (3)

wherein $A_{31}$ and $A_{32}$ each independently represent a hetero atom selected from the group consisting of an oxygen atom, a nitrogen atom and a sulfur atom; $Y_{31}$ and $Y_{32}$ each independently represent a hydrogen atom or a monovalent substituent; at least one of $Y_{31}$ and $Y_{32}$ represents a substituent having a Hammett substituent constant σp of 0.2 or more; $Y_{31}$ and $Y_{32}$ may bind to each other to form a ring; and (D) represents a group of atoms necessary for forming a five- or six-membered ring with the carbon atoms.

<9> The polymer material described in the above item <8>, wherein the compound represented by formula (3) is a compound represented by formula (4):

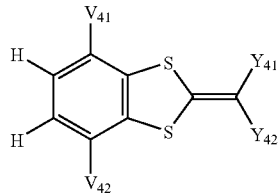

Formula (4)

wherein $Y_{41}$ and $Y_{42}$ each independently represent a monovalent substituent; at least one of $Y_{41}$ and $Y_{42}$ represents a cyano group, and the other represents a substituted or unsubstituted alkylcarbonyl group, a substituted or unsubstituted arylcarbonyl group, a substituted or unsubstituted heterocyclic carbonyl group, a substituted or unsubstituted alkylsulfonyl group, or a substituted or unsubstituted arylsulfonyl group; and $V_{41}$ and $V_{42}$ each independently represent a hydrogen atom or a monovalent substituent.

<10> A compound represented by formula (5):

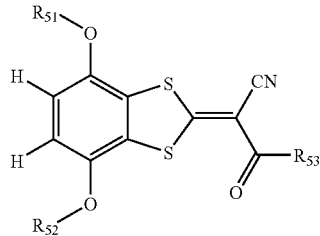

Formula (5)

wherein $R_{51}$ and $R_{52}$ each independently represent an unsubstituted alkyl group having 1 to 18 carbon atoms, or an unsubstituted alkylcarbonyl group having 2 to 18 carbon atoms; $R_{53}$ represents an unsubstituted alkyl group having 2 to 18 carbon atoms, or an unsubstituted aryl group having 6 to 10 carbon atoms.

<11> An ultraviolet absorbent, comprising the compound described in the above item <10>.

<12> A polymer material, comprising the ultraviolet absorbent described in the above item <11>.

Other and further features and advantages of the invention will appear more fully from the following description.

BEST MODE FOR CARRYING OUT INVENTION

Hereinafter, the present invention will be described in detail. The compound for use in the present invention is a compound represented by formula (2). Hereinafter, the compound represented by formula (2) will be described.

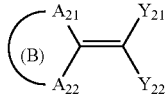

Formula (2)

(In formula (2), $A_{21}$ and $A_{22}$ each independently represent an atom other than hydrogen atom and carbon atom; $Y_{21}$ and $Y_{22}$ each independently represent a hydrogen atom or a monovalent substituent; at least one of $Y_{21}$ and $Y_{22}$ represents a substituent having a Hammett substituent constant up of 0.2 or more; $Y_{21}$ and $Y_{22}$ may bind to each other to form a ring; and (B) represents a group of atoms necessary for forming a five- or six-membered ring with $A_{21}$, $A_{22}$ and the carbon atom.)

$A_{21}$ and $A_{22}$ each independently represent an atom other than hydrogen atom and carbon atom. Examples of $A_{21}$ and $A_{22}$ include boron, nitrogen, oxygen, fluorine, silicon, phosphorus, sulfur and selenium atoms.

Preferable examples of $A_{21}$ and $A_{22}$ include nitrogen, oxygen and sulfur. Of these atoms, sulfur is especially preferable. Preferable combinations of $A_{21}$ and $A_{22}$ are oxygen-nitrogen, nitrogen-sulfur, nitrogen-nitrogen or sulfur-sulfur. Especially preferable combination is sulfur-sulfur.

$Y_{21}$ and $Y_{22}$ each independently represent a hydrogen atom or a monovalent substituent. Examples of the monovalent substituent include a cyano group, a substituted or unsubstituted carbamoyl group, a substituted or unsubstituted sulfamoyl group, a nitro group, a substituted or unsubstituted acyl group, a substituted or unsubstituted alkylsulfonyl group, a substituted or unsubstituted arylsulfonyl group, a substituted or unsubstituted alkylsulfinyl group, a substituted or unsubstituted arylsulfinyl group, a substituted or unsubstituted alkoxycarbonyl group, a substituted or unsubstituted aryloxycarbonyl group, a substituted or unsubstituted alkyl group, a substituted or unsubstituted aryl group, and a substituted or unsubstituted heterocyclic group. The substituent may be further substituted, and multiple substituents, if present, may be the same as or different from each other. In the present case, the substituent is the above-described monovalent substituent. In addition, the substituents may bind to each other to form a ring.

Examples of $Y_{21}$ and $Y_{22}$ include a cyano group, a carbamoyl group having 1 to 10 carbon atoms (preferably 2 to 8 carbon atoms, more preferably 2 to 5 carbon atoms) (e.g., methylcarbamoyl, ethylcarbamoyl, morpholinocarbonyl), a sulfamoyl group having 0 to 10 carbon atoms (preferably 2 to 8 carbon atoms, more preferably 2 to 5 carbon atoms) (e.g., methylsulfamoyl, ethylsulfamoyl, piperidylsulfonyl), a nitro group, an acyl group having 1 to 20 carbon atoms (preferably 1 to 12 carbon atoms, more preferably 1 to 8 carbon atoms) (e.g., formyl, acetyl, benzoyl, trichloroacetyl), an alkylsulfonyl group having 1 to 20 carbon atoms (preferably 1 to 10 carbon atoms, more preferably 1 to 8 carbon atoms) and an arylsulfonyl group having 6 to 20 carbon atoms (preferably 6 to 10 carbon atoms) (e.g., methanesulfonyl, ethanesulfonyl, benzenesulfonyl), an alkylsulfinyl group having 1 to 20 carbon atoms (preferably 1 to 10 carbon atoms, more preferably 1 to 8 carbon atoms) and an arylsulfinyl group having 6 to 20 carbon atoms (preferably 6 to 10 carbon atoms) (e.g., methanesulfinyl, benzenesulfinyl), an alkoxycarbonyl group having 2 to 20 carbon atoms (preferably 2 to 12 carbon atoms, more preferably 2 to 8 carbon atoms) (e.g., methoxycarbonyl, ethoxycarbonyl, benzyloxycarbonyl), an aryloxycarbonyl group having 6 to 20 carbon atoms (preferably 6 to 12 carbon atoms, more preferably 6 to 8 carbon atoms) (e.g., phenoxycarbonyl), an unsubstituted alkyl group having 1 to 18 carbon atoms (preferably 1 to 10 carbon atoms, more preferably 1 to 5 carbon atoms) (e.g., methyl, ethyl, propyl, butyl), a substituted alkyl group having 1 to 18 carbon atoms (preferably 1 to 10 carbon atoms, more preferably 1 to 5 carbon atoms) (e.g., hydroxymethyl, trifluoromethyl, benzyl, carboxyethyl, ethoxycarbonylmethyl, acetylaminomethyl), a substituted or unsubstituted aryl group having 6 to 20 (preferably 6 to 15 carbon atoms, more preferably 6 to 10 carbon atoms) (e.g., phenyl, naphthyl, p-carboxyphenyl, p-nitrophenyl, 3,5-dichlorophenyl, p-cyanophenyl, m-fluorophenyl, p-tolyl, p-bromophenyl), and a substituted or unsubstituted heterocyclic group having 1 to 20 (preferably 2 to 10 carbon atoms, more preferably 4 to 6 carbon atoms) (e.g., pyridyl, 5-methylpyridyl, thienyl, furyl, morpholino, tetrahydrofurfuryl). The substituent may be further substituted, and multiple substituents, if present, may be the same as or different from each other. In the present case, the substituent is the above-described monovalent substituent. In addition, the substituents may bind to each other to form a ring.

As $Y_{21}$ and $Y_{22}$, it is preferable that at least one of $Y_{21}$ and $Y_{22}$ has a Hammett substituent constant σp value of 0.2 or more.

The expression "Hammett substituent constant $\sigma_p$ value" used herein will be briefly described. Hammett's rule is a rule of thumb advocated by L. P. Hammett in 1935 for quantitatively considering the effect of substituents on the reaction or equilibrium of benzene derivatives, and the appropriateness thereof is now widely recognized. The substituent constant determined in the Hammett's rule involves $\sigma_p$ value and $\sigma_m$ value. These values can be found in a multiplicity of general publications, and are detailed in, for example, "Lange's Handbook of Chemistry" 12th edition by J. A. Dean, 1979 (McGraw-Hill), "Kagaku no Ryoiki" special issue, No. 122, pp. 96 to 103, 1979 (Nankodo) and Chem. Rev., vol. 91, pp. 165 to 195, 1991. The substituent having a Hammett substituent constant σp of 0.2 or more in the present invention is an electron-withdrawing group. The σp value is preferably 0.25 or more, more preferably 0.3 or more, and particularly preferably 0.35 or more.

Examples thereof include a cyano group (0.66), a carboxyl group (—COOH: 0.45), an alkoxycarbonyl group (e.g. —COOMe: 0.45), an aryloxycarbonyl group (e.g. —COOPh: 0.44), a carbamoyl group (—CONH₂: 0.36), an alkylcarbonyl group (e.g. —COMe: 0.50), an arylcarbonyl group (e.g. —COPh: 0.43), an alkylsulfonyl group (e.g. —SO₂Me: 0.72), an arylsulfonyl group (e.g. —SO₂Ph: 0.68) and the like. In the present description, Me represents a methyl group and Ph represents a phenyl group. The values in parenthesis are the σp values of typical substituents, as extracted from Chem. Rev., 1991, vol. 91, p. 165 to 195.

$Y_{21}$ and $Y_{22}$ may bind to each other to form a ring. The σp values of $Y_{21}$ and $Y_{22}$ may not be specified when a ring is formed, but in the present invention, the σp values thereof when a ring is formed are defined, assuming that partial ring structures are substituted respectively as $Y_{21}$ and $Y_{22}$. For example, when a 1,3-indandione ring is formed, benzoyl groups are considered to be substituted respectively as $Y_{21}$ and $Y_{22}$.

Preferred examples of $Y_{21}$ and $Y_{22}$ include a cyano group, an alkylcarbonyl group, an arylcarbonyl group, an alkoxycarbonyl group, an aryloxycarbonyl, a carbamoyl group, a sulfinyl group, a sulfonyl group and a sulfamoyl group.

It is especially preferable that at least one of $Y_{21}$ and $Y_{22}$ is a cyano group, and the other is an alkylcarbonyl group, an arylcarbonyl group, a heterocyclic carbonyl group, an alkylsulfonyl group, or an arylsulfonyl group. It is preferable that $Y_{21}$ and $Y_{22}$ do not bind to each other to form any ring.

(B) represents a group of atoms necessary for forming a five- or six-membered ring with $A_{21}, A_{22}$ and the carbon atom.

As a ring formed by (B) with $A_{21}, A_{22}$ and the carbon atom, a five- or six-membered ring is preferable. Specifically, examples of the ring include a pyrimidine ring, an imidazolidine ring, an imidazoline ring, an oxazoline ring, a thiazoline ring, and a dithiol ring. These rings may have a monovalent substituent. Further, these rings may form a condensed ring with an aromatic ring or the like.

As the ring formed by (B), an imidazoline ring, an oxazoline ring, a thiazoline ring, a dithiol ring, or a benzo-condensed ring thereof is preferable. More preferable ring is a benzodithiol ring, a benzoxazoline ring, a benzothiazoline ring, or a benzoimidazoline ring. Especially preferable ring is a benzodithiol ring.

A preferable combination of the substituents in the formula (2) is such a combination that at least one of $Y_{21}$ and $Y_{22}$ is a cyano group, and the other is an alkylcarbonyl group, an arylcarbonyl group, a heterocyclic carbonyl group, an alkylsulfonyl group, or an arylsulfonyl group; both $A_{21}$ and $A_{22}$ are a sulfur atom; and the ring formed by (B) is a benzodithiole ring.

The compound represented by formula (2) is preferably a compound represented by formula (3). Hereinafter, the compound represented by formula (3) will be described.

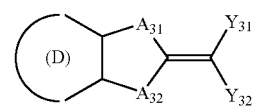

Formula (3)

(In formula (3), $A_{31}$ and $A_{32}$ each independently represent a hetero atom selected from the group consisting of an oxygen atom, a nitrogen atom and a sulfur atom; $Y_{31}$ and $Y_{32}$ each independently represent a hydrogen atom or a monovalent substituent; at least one of $Y_{31}$ and $Y_{32}$ represents a substituent having a Hammett substituent constant sap of 0.2 or more; $Y_{31}$ and $Y_{32}$ may bind to each other to form a ring; and (D) represents a group of atoms necessary for forming a five- or six-membered ring with the carbon atoms.)

$A_{31}$ and $A_{32}$ each independently represent a hetero atom selected from the group consisting of an oxygen atom, a nitrogen atom and a sulfur atom; preferably a sulfur atom. Preferable combinations of $A_{31}$ and $A_{32}$ are oxygen-nitrogen, nitrogen-sulfur, nitrogen-nitrogen or sulfur-sulfur. Especially preferable combination is sulfur-sulfur.

$Y_{31}$ and $Y_{32}$ each independently represent a hydrogen atom or a monovalent substituent. Examples of the monovalent substituent include a cyano group, a substituted or unsubstituted carbamoyl group, a substituted or unsubstituted sulfamoyl group, a nitro group, a substituted or unsubstituted acyl group, a substituted or unsubstituted alkylsulfonyl group, a substituted or unsubstituted arylsulfonyl group, a substituted or unsubstituted alkylsulfinyl group, a substituted or unsubstituted arylsulfinyl group, a substituted or unsubstituted alkoxycarbonyl group, a substituted or unsubstituted aryloxycarbonyl group, a substituted or unsubstituted alkyl group, a substituted or unsubstituted aryl group, and a substituted or unsubstituted heterocyclic group. Herein, at least one of $Y_{31}$ and $Y_{32}$ represents a substituent having a Hammett substituent constant σp of 0.2 or more. Examples of the substituent having a Hammett substituent constant σp of 0.2 or more include a cyano group, an alkylcarbonyl group, an arylcarbonyl group, an alkoxycarbonyl group, an aryloxycarbonyl group, a carbamoyl group, a sulfinyl group, a sulfonyl group and a sulfamoyl group.

It is especially preferable that at least one of $Y_{31}$ and $Y_{32}$ is a cyano group, and the other is a substituted or unsubstituted alkylcarbonyl group, a substituted or unsubstituted arylcarbonyl group, a substituted or unsubstituted heterocyclic carbonyl group, a substituted or unsubstituted alkylsulfonyl group, or a substituted or unsubstituted arylsulfonyl group.

(D) represents a group of atoms necessary for forming a five- or six-membered ring with the carbon atoms.

Specific examples of the ring formed by (D) include cycloalkanes such as cyclohexane and cyclopentane; aryls such as benzene; and heterocycles such as a pyridine ring, a pyrrole ring, a thiophene ring, a thiazole ring, an oxazole ring, and a pyrazole ring, and benzo-fused rings thereof. The ring is more preferable is a benzene ring.

A preferable combination of the substituents in the formula (3) is such a combination that at least one of $Y_{31}$ and $Y_{32}$ is a cyano group, and the other is a substituted or unsubstituted alkylcarbonyl group, a substituted or unsubstituted arylcarbonyl group, a substituted or unsubstituted heterocyclic carbonyl group, a substituted or unsubstituted alkylsulfonyl group, or a substituted or unsubstituted arylsulfonyl group; both $A_{31}$ and $A_{32}$ are a sulfur atom; and the ring formed by (D) is a benzene ring thereby forming a benzodithiole ring with $A_{31}$ and $A_{32}$.

The compound represented by formula (3) is preferably a compound represented by formula (4). Hereinafter, the compound represented by formula (4) will be described.

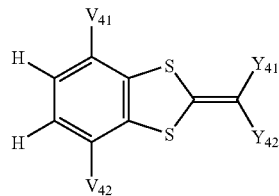

Formula (4)

(In formula (4), $Y_{41}$ and $Y_{42}$ each independently represent a monovalent substituent; at least one of $Y_{41}$ and $Y_{42}$ represents a cyano group, and the other represents a substituted or unsubstituted alkylcarbonyl group, a substituted or unsubstituted arylcarbonyl group, a substituted or unsubstituted heterocyclic carbonyl group, a substituted or unsubstituted alkylsulfonyl group, or a substituted or unsubstituted arylsulfonyl group.)

It is preferable that at least one of $Y_{41}$ and $Y_{42}$ is a cyano group, and the other is a substituted or unsubstituted alkylcarbonyl group, a substituted or unsubstituted arylcarbonyl group, or a substituted or unsubstituted heterocyclic carbonyl group. It is especially preferable that at least one of $Y_{41}$ and $Y_{42}$ is a cyano group, and the other is a substituted or unsubstituted alkylcarbonyl group, or a substituted or unsubstituted arylcarbonyl group. Further, it is preferable that $Y_{41}$ and $Y_{42}$ do not bind to each other to form any ring with other atom. It is further preferable that at least one of $Y_{41}$ and $Y_{42}$ is a cyano group, and the other is a substituted or unsubstituted alkylcarbonyl group having 3 to 18 carbon atoms, or a substituted or unsubstituted arylcarbonyl group having 7 to 18 carbon atoms.

$V_{41}$ and $V_{42}$ each independently represent a hydrogen atom or a monovalent substituent. Examples of the monovalent substituent include a halogen atom, a mercapto group, a cyano group, a carboxyl group, a phosphoric acid group, a sulfo group, a hydroxy group, a carbamoyl group, a sulfamoyl group, a nitro group, an alkoxy group, an aryloxy group, an acyl group, an acyloxy group, an acylamino group, a sulfonyl group, a sulfinyl group, a sulfonylamino group, an amino group, a substituted amino group, an ammonium group, a hydrazino group, a ureido group, an imido group, an alkyl- or aryl-thio group, a substituted or unsubstituted alkenylthio group, an alkoxycarbonyl group, an aryloxycarbonyl group, an unsubstituted alkyl group, a substituted alkyl group, a substituted or unsubstituted aryl group, and a substituted or unsubstituted heterocyclic group. Specific examples of these substituents include those groups recited as examples of $Y_{41}$ and $Y_{42}$. The substituent may be further substituted, and multiple substituents, if present, may be the same as or different from each other. In the present case, the substituent is the above-described monovalent substituent. In addition, the substituents may bind to each other to form a ring.

$V_{41}$ and $V_{42}$ each are preferably a cyano group, a nitro group, a hydroxyl group, an alkoxy group, an aryloxy group, or an acyloxy group; and particularly preferably an alkoxy group, an aryloxy group, or an acyloxy group.

A preferable combination of the substituents in the formula (4) is such a combination that at least one of $Y_{41}$ and $Y_{42}$ is a cyano group, and the other is a substituted or unsubstituted alkylcarbonyl group having 3 to 18 carbon atoms, or a substituted or unsubstituted arylcarbonyl group having 7 to 18 carbon atoms; and both $V_{41}$ and $V_{42}$ are an alkoxy group, an aryloxy group, or an acyloxy group.

Next, the compound represented by formula (5) will be described in detail.

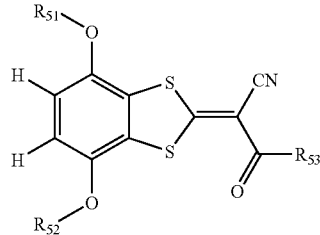

Formula (5)

(In formula (5), $R_{51}$ and $R_{52}$ each independently represent an unsubstituted alkyl group having 1 to 18 carbon atoms, or an unsubstituted alkylcarbonyl group having 2 to 18 carbon atoms; and $R_{53}$ represents an unsubstituted alkyl group having 2 to 18 carbon atoms, or an unsubstituted aryl group having 6 to 10 carbon atoms.)

$R_{51}$ and $R_{52}$ each independently represent an unsubstituted alkyl group having 1 to 18 carbon atoms, or an unsubstituted alkylcarbonyl group having 2 to 18 carbon atoms. In particular, methyl, acetyl, 2-ethylhexyl and 2-ethylhexanoyl groups are preferable, and 2-ethylhexyl and 2-ethylhexanoyl groups are particularly preferable.

$R_{53}$ represents an unsubstituted alkyl group having 2 to 18 carbon atoms, or an unsubstituted aryl group having 6 to 10 carbon atoms. The unsubstituted alkyl group is preferably an ethyl, propyl, iso-propyl, butyl, or tert-butyl group; particularly preferably a tert-butyl group. The unsubstituted aryl group is preferably a phenyl or naphthyl group, particularly preferably a phenyl group.

A preferable combination of the substituents in formula (5) is such a combination that both $R_{51}$ and $R_{52}$ are a 2-ethylhexyl group or a 2-ethylhexanoyl groups, and $R_{53}$ is a tert-butyl or phenyl group.

A typical synthetic example for the compound represented by any one of formulae (2) to (5) above will be described below. The compound represented by any one of formulae (2) to (5) in the present invention can be synthesized according to any one of the methods described or cited in Journal of Chemical Crystallography, 27, 1997, p. 516, right column, line 3 to p. 520, right column, line 15; Liebigs Annalen der Chemie, 726, p. 106, line 15 to p. 109, line 37; JP-A-49-1115, p. 3, left column, line 7 to p. 5, left column, line 8; Bioorganic & Medicinal Chemistry Letters, 7, 1997, p. 652, lines 9 to 19; Journal of Organic Chemistry, 43, 1978, p. 2153, left column, lines 2 to 12; JP-A-4-338759, p. 4, left column, line 2 to p. 5, left column, line 2; JP-A-3-54566, p. 7, left column, line 6 to p. 8, left column, line 10; Synthesis, 1986, p. 968, left column, lines 1 to 22, or a method similar to that.

Hereinafter, typical preferred examples of the compound represented by any one of formulae (2) to (5) will be described below, but the present invention is not restricted thereby. Et represents an ethyl group and Pr represents a propyl group in the following compounds.

Examples of the Compound Corresponding to that Represented by Formula (5)

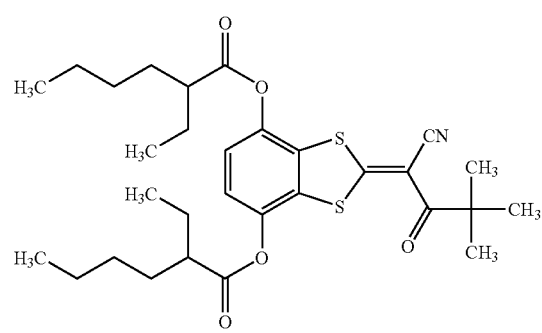
(S-01)

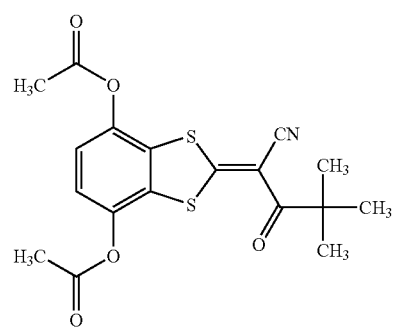
(S-02)

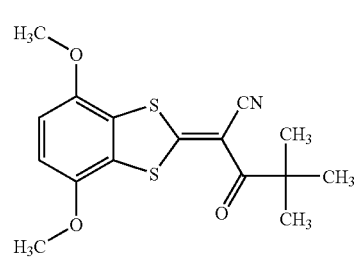
(S-03)

(S-04)

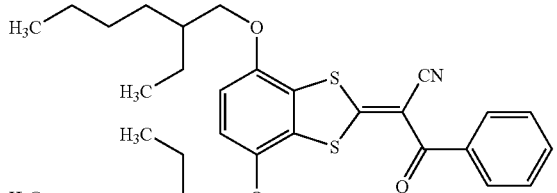
(S-05)

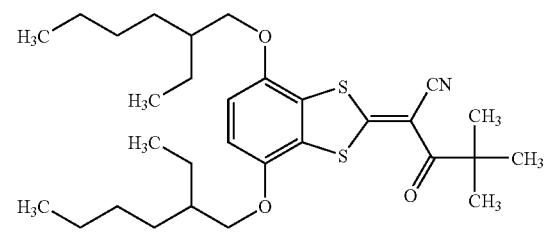
(S-06)

Examples of the Compound Corresponding to that Represented by not Formula (5) but Formula (4)

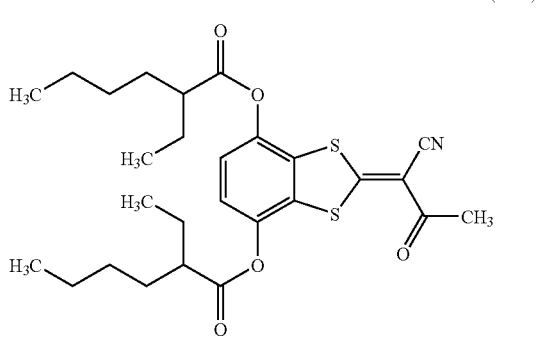
(S-07)

(S-08)

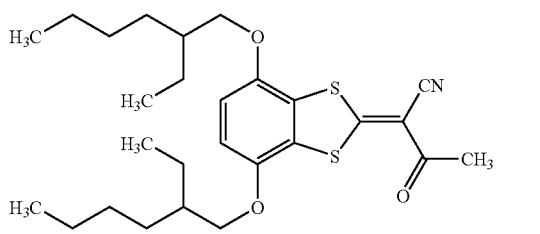
(S-09)

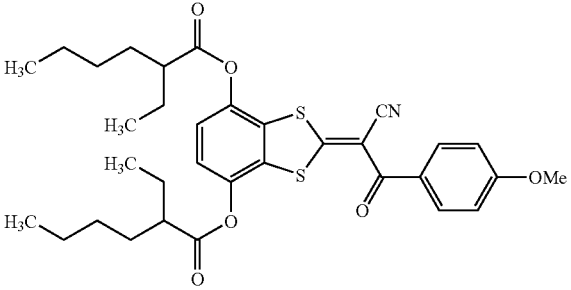

(S-10)
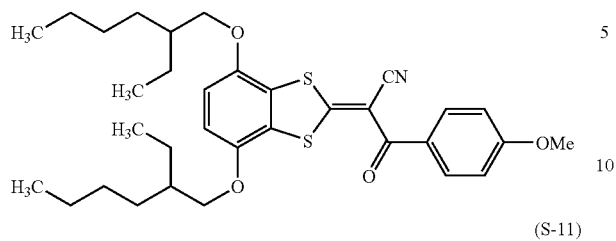
(S-11)
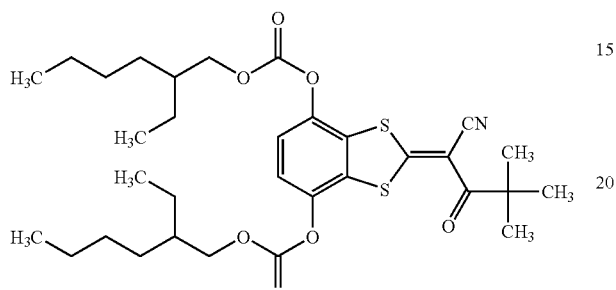
(S-12)
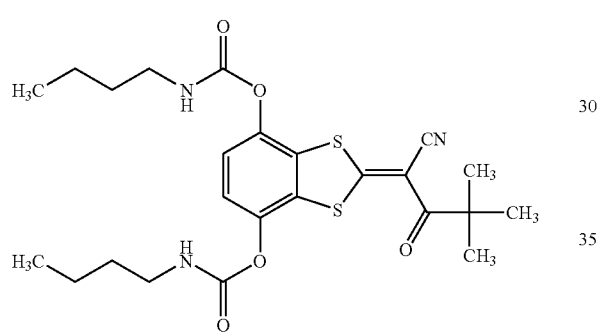
(S-13)
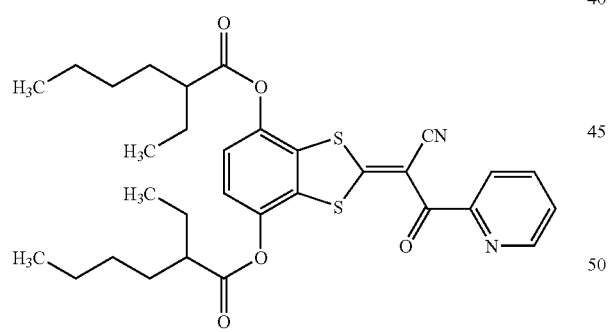
(S-14)
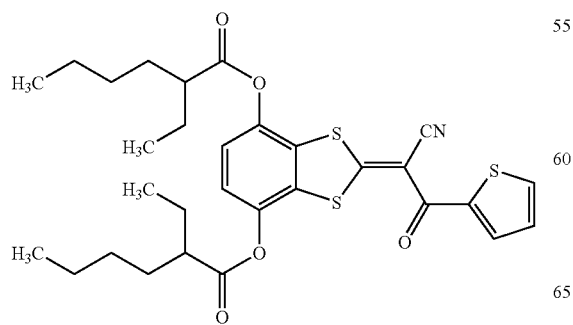
(S-15)
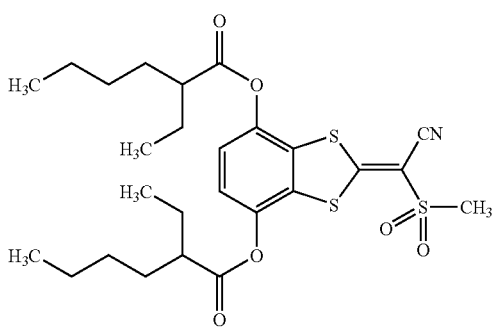
(S-16)
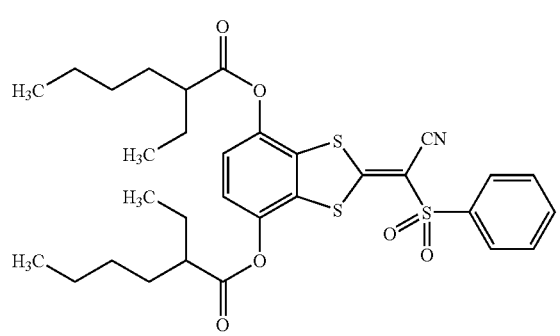
Examples of the Compound Corresponding to that Represented by not Formula (4) but Formula (3)
(S-17)
(S-18)
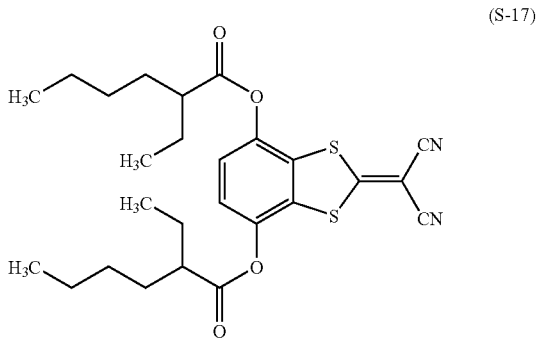

-continued

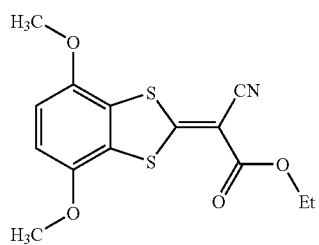 (S-19)

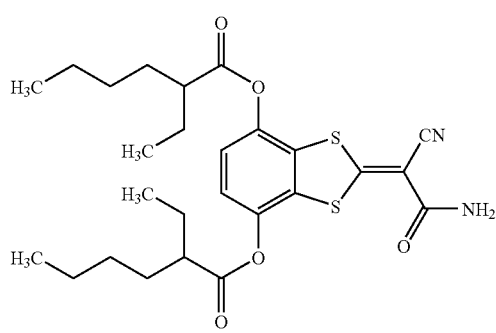 (S-20)

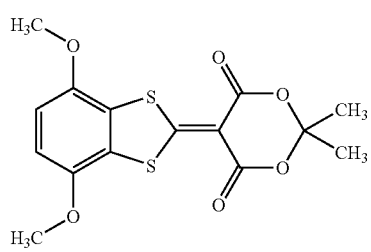 (S-21)

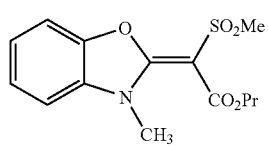 (S-22)

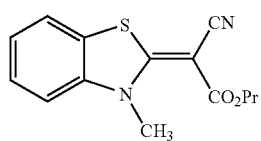 (S-23)

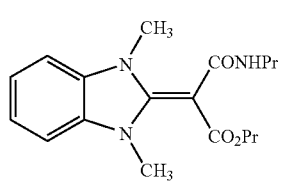 (S-24)

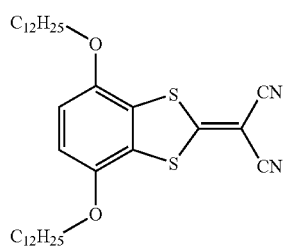 (S-25)

-continued

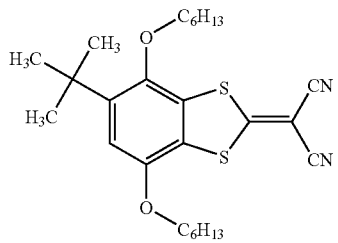 (S-26)

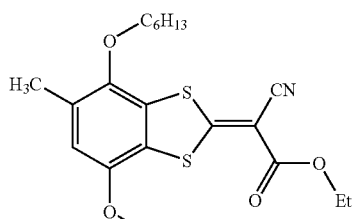 (S-27)

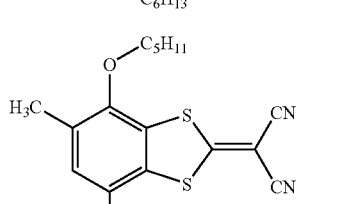 (S-28)

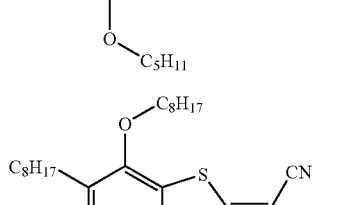 (S-29)

Examples of the Compound Corresponding to that Represented by not Formula (3) but Formula (2)

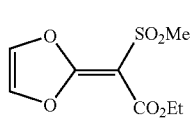 (S-30)

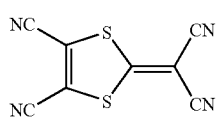 (S-31)

The compound represented by any one of formulae (2) to (5) may have a tautomer, depending on its structure and the environment to which the compound is exposed. In the present specification, only a typical tautomer is described, but other tautomers different from that described in the present specification are also included in the compound that can be used in the present invention compound.

The compound represented by any one of formulae (2) to (5) may have an isotopic element (such as $^2H$, $^3H$, $^{13}C$, $^{15}N$, $^{17}O$, or $^{18}O$).

A polymer having the structure of the compound represented by any one of formulae (2) to (5) in its recurring unit as the ultraviolet absorptive group can also be used favorably in the present invention. Hereinafter, examples of the recurring unit containing the structure of the compound represented by any one of formula (2) to (5) will be shown.

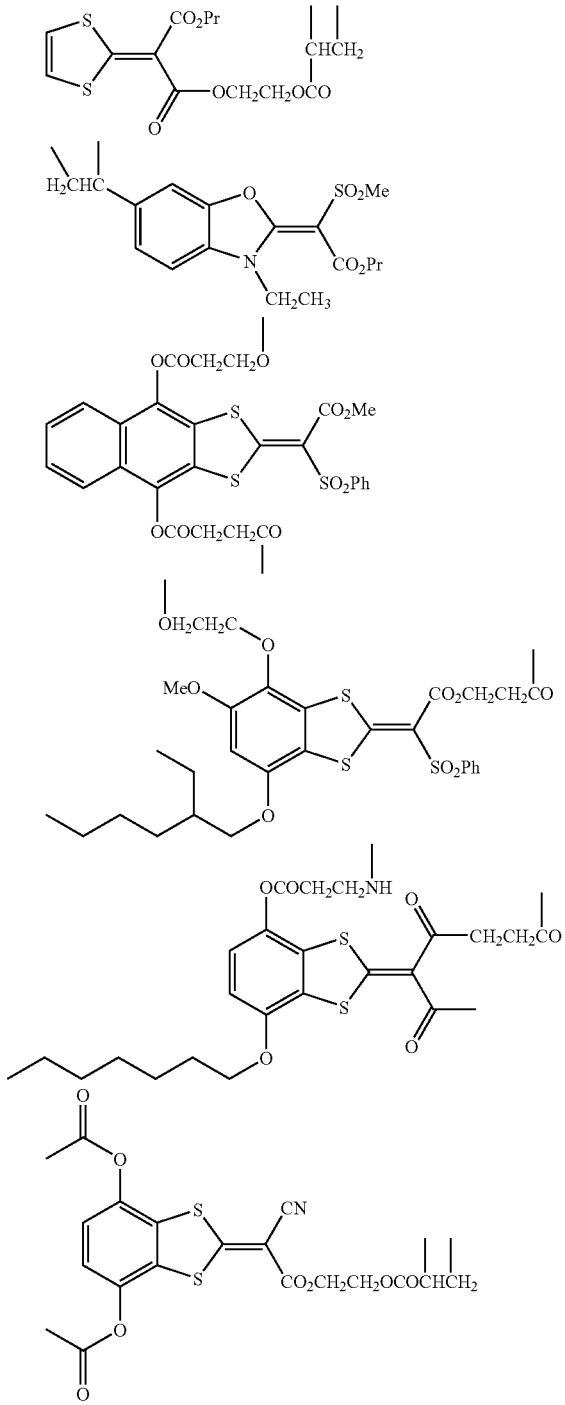

The polymer may be a homopolymer having one kind of recurring unit or a copolymer having two or more kinds of recurring units. It may be a copolymer having another recurring unit additionally. Hereinafter, examples of the other recurring unit are shown.

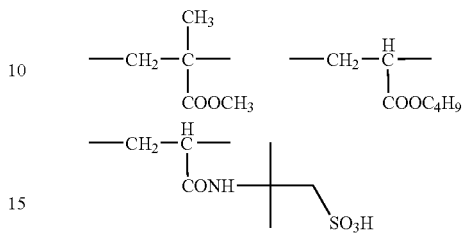

The polymer composition is used in preparation of the polymer material according to the present invention. The polymer composition for use in the present invention contains a polymer substance described below and the compound represented by any one of formulae (2) to (5).

The compound represented by any one of formulae (2) to (5) is contained in the polymer substance in various methods. When the compound represented by any one of formulae (2) to (5) is compatible with the polymer substance, the compound represented by any one of formulae (2) to (5) may be added to the polymer substance directly. The compound represented by any one of formulae (2) to (5) may be dissolved in a cosolvent compatible with the polymer substance, and then the obtained solution be added to the polymer substance. The compound represented by any one of formulae (2) to (5) may be dispersed in a polymer, and the obtained dispersion be added to the polymer substance.

The method of adding the compound represented by any one of formulae (2) to (5) is determined, by reference to the description in JP-A-58-209735, JP-A-63-264748, JP-A-4-191851, JP-A-8-272058, and British Patent No. 2016017A.

In the present invention, two or more kinds of compounds in the present invention different in structure may be used in combination. Alternatively, the compound in the present invention and one or more kinds of ultraviolet absorbents different in structure may be used in combination. Two kinds (preferably three kinds) of ultraviolet absorbents when used in combination absorb ultraviolet ray in a wider wavelength range. In addition, the use of two or more kinds of ultraviolet absorbents in combination has a function to stabilize the dispersion state. Any ultraviolet absorbent having a structure other than that of ultraviolet absorbent in the present invention may be used. Examples thereof include those described, for example, in Yasuichi Okatsu Ed., "Development of Polymer Additives and Environmental Measures" (CMC Publishing, 2003), Chapter 2; and Toray Research Center Inc., Technical Survey Dept., Ed., "New Trend of Functional Polymer Additives" (Toray Research Center Inc., 1999), Chapter 2.3.1. Examples thereof include ultraviolet absorbing structures such as triazine-based, benzotriazole-based, benzophenone-based, merocyanine-based, cyanine-based, dibenzoylmethane-based, cinnamic acid-based, acrylate-based, benzoic ester-based, and oxalic diamide-based compounds. Specific examples thereof are described, for example, in Fine Chemicals, 2004, May, p. 28 to 38; Toray Research Center Inc., Technical Survey Dept., Ed., "New Trend of Functional Polymer Additives" (Toray Research Center Inc., 1999), p. 96 to 140; and Yasuichi Okatsu Ed., "Development of Polymer Additives and Environmental Measures" (CMC Publishing, 2003), p. 54 to 64.

Among these, preferable are benzotriazole-based, benzophenone-based, salicylic acid-based, acrylate-based, and triazine-based compounds. More preferable are benzotriazole-based, benzophenone-based, and triazine-based compounds. Particularly preferable are benzotriazole-based and triazine-based compounds.

The polymer material according to the present invention may contain multiple UV absorbents represented by formula (2). The UV absorbent may be used in combination with a known absorbent different in the structure.

The benzotriazole-based compound is preferably a compound having an effective absorption wavelength of approximately 270 to 380 nm that is represented by formula (IIa) or (IIb). The compound represented by formula (IIa) or (IIb) will be described in detail.

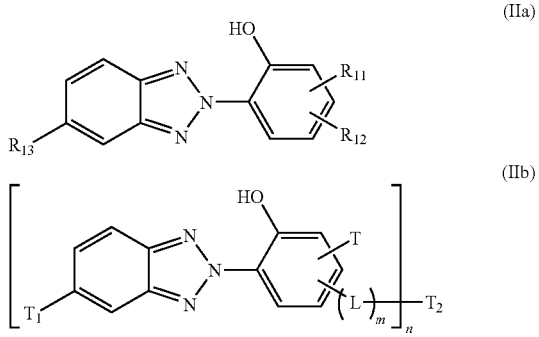

(In formula (IIa), $R_{11}$ represents a hydrogen atom, a substituted or unsubstituted alkyl group, a substituted or unsubstituted cycloalkyl group, or a substituted or unsubstituted aryl group, $R_{12}$ represents a hydrogen atom, a halogen atom, a substituted or unsubstituted alkyl group, or a substituted or unsubstituted aryl group, and $R_{13}$ represents a hydrogen atom, a halogen atom, a substituted or unsubstituted alkyl group, a substituted or unsubstituted alkoxy group, or —COOR$_{14}$ group (herein, R$_{14}$ represents a hydrogen atom, a substituted or unsubstituted alkyl group or a substituted or unsubstituted aryl group.))

(In formula (IIb),

T represents a hydrogen atom or a substituted or unsubstituted alkyl group, $T_1$ represents a hydrogen atom, a halogen atom, a substituted or unsubstituted alkyl group, a substituted or unsubstituted aryl group, or a substituted or unsubstituted alkoxy group, L represents a divalent linking group or a single bond;

m represents 0 or 1;

n represents an integer of 1 to 4; and when n is 1, $T_2$ represents a halogen atom, a substituted or unsubstituted alkyl group or a substituted or unsubstituted aryl group; when n is 2, $T_2$ represents a divalent substituent; when n is 3, $T_2$ represents a trivalent substituent; and when n is 4, $T_2$ represents a tetravalent substituent.)

(Formula (IIa))

$R_{11}$ represents a hydrogen atom, a substituted or unsubstituted alkyl group, a substituted or unsubstituted cycloalkyl group or a substituted or unsubstituted aryl group.

$R_{11}$ is preferably a substituted or unsubstituted alkyl group having 1 to 18 carbon atoms, a substituted or unsubstituted cycloalkyl group having 5 to 18 carbon atoms or a substituted or unsubstituted aryl group having 6 to 24 carbon atoms; and particularly preferably a substituted or unsubstituted alkyl group having 1 to 18 carbon atoms or a substituted or unsubstituted alkyl group having 1 to 18 carbon atoms.

The substituted alkyl group, the substituted cycloalkyl group, and the substituted aryl group each are referred to as an alkyl group, a cycloalkyl group, and an aryl group, each of which has a monovalent substituent at an arbitrary position thereof, respectively. Examples of the monovalent substituent include a halogen atom (e.g., fluorine atom, chlorine atom, bromine atom, and iodine atom), a straight-chain or branched alkyl group having 1 to 20 carbon atoms (preferably 1 to 10 carbon atoms) (e.g., methyl, ethyl), an aryl group having 6 to 20 carbon atoms (preferably 6 to 10 carbon atoms) (e.g., phenyl, naphthyl), a cyano group, a carboxyl group, an alkoxycarbonyl group having 1 to 20 carbon atoms (preferably 1 to 10 carbon atoms) (e.g., methoxycarbonyl), an aryloxycarbonyl group having 6 to 20 carbon atoms (preferably 6 to 10 carbon atoms) (e.g., phenoxycarbonyl), a substituted or unsubstituted carbamoyl group having 0 to 20 carbon atoms (preferably 0 to 10 carbon atoms) (e.g., carbamoyl, N-phenylcarbamoyl, N,N-dimethylcarbamoyl), an alkylcarbonyl group having 1 to 20 carbon atoms (preferably 1 to 10 carbon atoms) (e.g., acetyl), an arylcarbonyl group having 6 to 20 carbon atoms (preferably 6 to 10 carbon atoms) (e.g., benzoyl), a nitro group, a substituted or unsubstituted amino group having 0 to 20 carbon atoms (preferably 0 to 10 carbon atoms) (e.g., amino, dimethylamino, anilino), an acylamino group having 1 to 20 carbon atoms (preferably 1 to 10 carbon atoms) (e.g., acetamido, ethoxycarbonylamino), a sulfonamido group having 0 to 20 carbon atoms (preferably 0 to 10 carbon atoms) (e.g., methanesulfonamido), an imido group having 2 to 20 carbon atoms (preferably 2 to 10 carbon atoms) (e.g., succinimido, phthalimido), an imino group having 1 to 20 carbon atoms (preferably 1 to 10 carbon atoms) (e.g., benzylideneamino), a hydroxy group, an alkoxy group having 1 to 20 carbon atoms (preferably 1 to 10 carbon atoms) (e.g., methoxy), an aryloxy group having 6 to 20 carbon atoms (preferably 6 to 10 carbon atoms) (e.g., phenoxy), an acyloxy group having 1 to 20 carbon atoms (preferably 1 to 10 carbon atoms) (e.g., acetoxy), an alkylsulfonyloxy group having 1 to 20 carbon atoms (preferably 1 to 10 carbon atoms) (e.g., methanesulfonyloxy), an arylsulfonyloxy group having 6 to 20 carbon atoms (preferably 6 to 10 carbon atoms) (e.g., benzenesulfonyloxy), a sulfo group, a substituted or unsubstituted sulfamoyl group having 0 to 20 carbon atoms (preferably 0 to 10 carbon atoms) (e.g., sulfamoyl, N-phenylsulfamoyl), an alkylthio group having 1 to 20 carbon atoms (preferably 1 to 10 carbon atoms) (e.g., methylthio), an arylthio group having 6 to 20 carbon atoms (preferably 6 to 10 carbon atoms) (e.g., phenylthio), an alkylsulfonyl group having 1 to 20 carbon atoms (preferably 1 to 10 carbon atoms) (e.g., methansulfonyl), an arylsulfonyl group having 6 to 20 carbon atoms (preferably 6 to 10 carbon atoms) (e.g., benzenesulfonyl), and a four- to seven-membered (preferably five- to six-membered) heterocyclic group (e.g., pyridyl, morpholino).

$R_{12}$ represents a hydrogen atom, a halogen atom, a substituted or unsubstituted alkyl group or a substituted or unsubstituted aryl group. $R_{12}$ is preferably a hydrogen atom, a chlorine atom, a substituted or unsubstituted alkyl group having 1 to 18 carbon atoms, a substituted or unsubstituted cycloalkyl group having 5 to 18 carbon atoms or a substituted or unsubstituted aryl group having 6 to 24 carbon atoms; and particularly preferably a hydrogen atom, a chlorine atom, a substituted or unsubstituted alkyl group having 1 to 18 carbon atoms or a substituted or unsubstituted aryl group having 6 to 24 carbon atoms.

$R_{13}$ represents a hydrogen atom, a halogen atom, a substituted or unsubstituted alkyl group, a substituted or unsubstituted alkoxy group or —$COOR_{14}$ group (herein, $R_{14}$ represents a hydrogen atom, a substituted or unsubstituted alkyl group or a substituted or unsubstituted aryl group). $R_{13}$ is preferably a hydrogen atom, a chlorine atom, a substituted or unsubstituted alkyl group having 1 to 18 carbon atoms, a substituted or unsubstituted alkoxy group having 1 to 18 carbon atoms, or —$COOR_{14}$ group (herein, $R_{14}$ represents a hydrogen atom, a substituted or unsubstituted alkyl group having 1 to 18 carbon atoms or a substituted or unsubstituted aryl group having 6 to 24 carbon atoms).

$R_{11}$ and $R_{12}$ may be substituted at an arbitrary position of the benzene ring. The substitution at 2- or 4-position to a hydroxyl group is preferable.

(Formula (IIb))

T represents a hydrogen atom or a substituted or unsubstituted alkyl group. T is preferably a hydrogen atom or a substituted or unsubstituted alkyl group having 1 to 18 carbon atoms.

$T_1$ represents a hydrogen atom, a halogen atom, a substituted or unsubstituted alkyl group, a substituted or unsubstituted aryl group or a substituted or unsubstituted alkoxy group. $T_1$ is preferably a hydrogen atom, a chlorine atom, a substituted or unsubstituted alkyl group having 1 to 18 carbon atoms, a substituted or unsubstituted aryl group having 6 to 24 carbon atoms or substituted or unsubstituted alkoxy group having 1 to 18 carbon atoms.

-L- represents a divalent linking group or a single bond. m represents 0 or 1.

The case where m is 0 (zero) means that $T_2$ directly bonds with the benzene ring without involving L, that is -L- represents a single bond.

The divalent linking group -L- is explained. -L- is a divalent substituent represented by formula (a).

$$-(L_1)_{m1}\text{-}(L_2)_{m2}\text{-}(L_3)_{m3}\text{-}(L_4)_{m4}\text{-}(L_5)_{m5}\text{-} \quad \text{Formula (a)}$$

In formula (a), m1, m2, m3, m4 and m5 each represent an integer of 0 to 2.

$L_1$, $L_2$, $L_3$, $L_4$ and $L_5$ each independently represent —CO—, —O—, —$SO_2$—, —SO—, —$NR_L$—, a substituted or unsubstituted divalent alkyl group, a substituted or unsubstituted divalent alkenyl group, or a substituted or unsubstituted divalent aryl group. $R_L$ represents a hydrogen atom, a substituted or unsubstituted alkyl group or a substituted or unsubstituted aryl group.

Examples of $R_L$ include a hydrogen atom, a methyl group, an ethyl group, a propyl group, a hexyl group, an octyl group, a phenyl group, and a naphthyl group. The group may be substituted with one or more monovalent substituents at any position of the alkyl or aryl group. The monovalent substituent is, for example, a monovalent substituent described above. $R_L$ is preferably a substituted or unsubstituted alkyl group having 3 to 20 carbon atoms or a substituted or unsubstituted aryl group having 6 to 14 carbon atoms; and more preferably a substituted or unsubstituted alkyl group having 6 to 12 carbon atoms or a substituted or unsubstituted aryl group having 6 to 10 carbon atoms.

Preferred examples of the divalent substituent -L- include —O—CO—$C_2H_4$—CO—O—, —O—CO—$C_3H_6$—, —NH—CO—$C_3H_6$—CO—NH—, —NH—CO—$C_4H_8$—, —$CH_2$—, —$C_2H_4$—, —$C_3H_6$—, —$C_4H_8$—, —$C_5H_{10}$—, —$C_8H_{16}$—, —$C_4H_8$—CO—O—, —$C_6H_4$—$C_6H_4$— and —NH—$SO_2$—$C_3H_6$—.

In formula (IIb), n represents an integer of 1 to 4.

When n is 1, $T_2$ represents a halogen atom, a substituted or unsubstituted alkyl group or a substituted or unsubstituted aryl group. When n is 1, $T_2$ is preferably a chlorine atom, a substituted or unsubstituted alkyl group having 1 to 18 carbon atoms, or a substituted or unsubstituted aryl group having 6 to 24 carbon atoms.

When n is 2, $T_2$ represents a divalent substituent. When n is 2, examples of T include the same examples as the above-described divalent substituent -L-. When n is 2, T is preferably —$CH_2$—, —O—CO—$C_2H_4$—CO—O—, or —NH—CO—$C_3H_6$—CO—NH—.

When n is 3, $T_2$ represents a trivalent substituent. The trivalent substituent is explained. Specifically, the trivalent substituent is a trivalent alkyl group, a trivalent aryl group, or a substituent represented by the following formula.

The trivalent substituent is preferably a trivalent alkyl group having 1 to 8 carbon atoms, a trivalent aryl group having 6 to 14 carbon atoms, or a substituent represented by the following formula.

When n is 4, $T_2$ represents a tetravalent substituent. The tetravalent substituent is explained. Specifically, the tetravalent substituent is a tetravalent alkyl group, or a tetravalent aryl group. Among the tetravalent substituents, a tetravalent alkyl group having 1 to 8 carbon atoms and a tetravalent aryl group having 6 to 14 carbon atoms are preferable.

In formula (IIb), it is especially preferable that n is 1 or 2.

Specifically, the components of the formula (IIb) are preferably combined as follows:

When n is 1, a preferable combination is that T is a hydrogen atom, or a substituted or unsubstituted alkyl group having 1 to 18 carbon atoms; $T_1$ is a hydrogen atom, a chlorine atom, a substituted or unsubstituted alkyl group having 1 to 18 carbon atoms, a substituted or unsubstituted aryl group having 6 to 24 carbon atoms, or a substituted or unsubstituted alkoxy group having 1 to 18 carbon atoms; L is —O—CO—$C_3H_6$—, —$CH_2$—, —$C_3H_6$—, —$C_5H_{10}$—, —$C_8H_{16}$—, —NH—CO—$C_4H_8$— or a single bond; and $T_2$ is a chlorine atom, a substituted or unsubstituted alkyl group having 1 to 18 carbon atoms, or a substituted or unsubstituted aryl group having 6 to 24 carbon atoms.

When n is 2, a preferable combination is that T is a hydrogen atom, or a substituted or unsubstituted alkyl group having 1 to 18 carbon atoms; $T_1$ is a hydrogen atom, a chlorine atom, a substituted or unsubstituted alkyl group having 1 to 18 carbon atoms, a substituted or unsubstituted aryl group having 6 to 24 carbon atoms, or a substituted or unsubstituted alkoxy group having 1 to 18 carbon atoms; L is —$CH_2$— or a single bond; and $T_2$ is —$CH_2$—, —O—CO—$C_2H_4$—CO—O— or NH—CO—$C_3H_6$—CO—NH—.

Further, when n is 2, a preferable another combination is that m is 0; T is a hydrogen atom, or a substituted or unsubstituted alkyl group having 1 to 18 carbon atoms; $T_1$ is a hydrogen atom, a chlorine atom, a substituted or unsubstituted alkyl group having 1 to 18 carbon atoms, a substituted or unsubstituted aryl group having 6 to 24 carbon atoms, or a substituted or unsubstituted alkoxy group having 1 to 18 carbon atoms; and $T_2$ is —$CH_2$—, —O—CO—$C_2H_4$—CO—O—, or —NH—CO—$C_3H_6$—CO—NH—.

Typical examples of the compound represented by formula (IIa) or (IIb) include 2-(2'-hydroxy-5'-methylphenyl)benzotriazole, 2-(2'-hydroxy-5'-t-butylphenyl)benzotriazole, 2-(2'-hydroxy-3'-t-butyl-5'-methylphenyl)-5-chlorobenzotriazole, 2-(2'-hydroxy-3',5'-di-t-butylphenyl)-5-chlorobenzotriazole, 2-(2'-hydroxy-3'-dodecyl-5'-methylphenyl)-5-chlorobenzotriazole, 2-(2'-hydroxy-3',5'-di-t-amylphenyl)benzotriazole, 2-(2'-hydroxy-5'-(1,1,3,3-tetramethylbutyl)phenyl)benzotriazole, 2-(2'-hydroxy-4'-octyloxyphenyl)benzotriazole, 2-(2'-hydroxy-3'-(3,4,5,6-tetrahydrophthalimidylmethyl)-5'-methylbenzyl)phenyl)benzotriazole, 2-(3'-sec-butyl-5'-t-butyl-2'-hydroxyphenyl)benzotriazole, 2-(3',5'-bis-(α,α-dimethylbenzyl)-2'-hydroxyphenyl)benzotriazole, 2-(3'-t-butyl-2'-hydroxy-5'-(2-octyloxycarbonylethyl)phenyl)-5-chloro-benzotriazole, 2-(3'-t-butyl-5'-(2-ethylhexyloxy)-carbonylethyl)-2'-hydroxyphenyl)-5-chloro-benzotriazole, 2-(3'-t-butyl-2'-hydroxy-5'-(2-methoxycarbonylethyl)phenyl)-5-chloro-benzotriazole, 2-(3'-t-butyl-2'-hydroxy-5'-(2-methoxycarbonylethyl)phenyl)benzotriazole, 2-(3'-t-butyl-2'-hydroxy-5'-(2-octyloxycarbonylethyl)phenyl)benzotriazole, 2-(3'-t-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-t-butyl-2'-hydroxy-5'-(2-isooctyloxycarbonylethyl) phenylbenzotriazole, 2,2'-methylene-bis[4-(1,1,3,3-tetramethylbutyl)-6-benzotriazole-2-ylphenol], ester exchange products of 2-[3'-t-butyl-5'-(2-methoxycarbonylethyl)-2'-hydroxyphenyl]-2H-benzotriazole and polyethylene glycol 300; and the compound represented by the following formula:

(wherein, R represents 3'-tert-butyl-4'-hydroxy-5'-2H-1-benzotriazol-2-ylphenyl, 2-[2'-hydroxy-3'-(α,α-dimethylbenzyl)-5'-(1,1,3,3-tetramethylbutyl)-phenyl]benzotriazole; 2-[2'-hydroxy-3'-(1,1,3,3-tetramethylbutyl)-5'-(α,α-dimethylbenzyl)-phenyl]benzotriazole or the like).

The triazine-based compound is preferably a compound having an effective absorption wavelength of approximately 270 to 380 nm that is represented by formula (III).

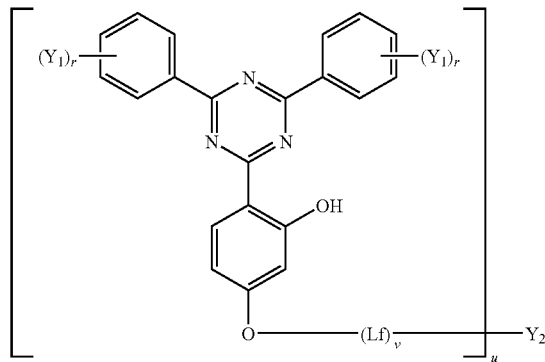

(In formula (III), the substituent $Y_1$ represents a hydrogen atom, a hydroxyl group, a substituted or unsubstituted alkyl group, a substituted or unsubstituted aryl group, or a substituted or unsubstituted alkoxy group;

Lf represents a divalent linking group or a single bond;

u represents 1 or 2;

v represents 0 or 1;

r represents an integer of 1 to 3; and when u is 1, $Y_2$ represents a hydrogen atom, a substituted or unsubstituted alkyl group or a substituted or unsubstituted aryl group; and when u is 2, $Y_2$ represents a divalent substituent.

$Y_1$ represents a hydrogen atom, a hydroxyl group, a substituted or unsubstituted alkyl group, a substituted or unsubstituted aryl group or a substituted or unsubstituted alkoxy group. $Y_1$ is preferably a hydrogen atom, a hydroxyl group, a substituted or unsubstituted alkyl group having 1 to 18 carbon atoms, a substituted or unsubstituted aryl group having 6 to 24 carbon atoms or a substituted or unsubstituted alkoxy group having 1 to 18 carbon atoms.

Lf represents a divalent linking group or a single bond. u represents 1 or 2. r represents an integer of 1 to 3, v represents 0 or 1. When v is 0, Lf represents a single bond.

The divalent linking group -Lf- is explained. The divalent linking group -Lf- is a divalent substituent represented by formula (b).

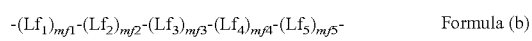

Formula (b)

In formula (b), mf1 to mf5 each represent an integer of 0 to 2.

$Lf_1$, $Lf_2$, $Lf_3$, $Lf_4$ and $Lf_5$ each independently represent —CO—, —O—, —$SO_2$—, —SO—, —$NRf_L$, a substituted or unsubstituted divalent alkyl group, a substituted or unsubstituted divalent alkenyl group, or a substituted or unsubstituted divalent aryl group. $Rf_L$ represents a hydrogen atom, a substituted or unsubstituted alkyl group or a substituted or unsubstituted aryl group.

Examples of $Rf_L$, include a hydrogen atom, a methyl group, an ethyl group, a propyl group, a hexyl group, an octyl group, a phenyl group, and a naphthyl group. The group may be substituted with one or more monovalent substituents at any position of the alkyl or aryl groups. The monovalent substituent is, for example, a monovalent substituent described above. $Rf_L$ is preferably a substituted or unsubstituted alkyl group having 3 to 20 carbon atoms or a substituted or unsubstituted aryl group having 6 to 14 carbon atoms; and more preferably a substituted or unsubstituted alkyl group having 6 to 12 carbon atoms or a substituted or unsubstituted aryl group having 6 to 10 carbon atoms.

Preferred examples of the divalent substituent -Lf- include —O—CO—$C_2H_4$—CO—O—, —O—CO—$C_3H_6$—, —NH—CO—$C_3H_6$—CO—NH—, —NH—CO—$C_4H_8$—, —$CH_2$—, —$C_2H_4$—, —$C_3H_6$—, —$C_4H_8$—, —$C_5H_{10}$—, —$C_8$—$H_{16}$—, —$C_4$—$H_8$—CO—O—, —$C_6H_4$—$C_6H_4$— and —NH—$SO_2$—$C_3H_6$—.

When u is 1, $Y_2$ represents a hydrogen atom, a substituted or unsubstituted alkyl group or a substituted or unsubstituted aryl group. When u is 1, $Y_2$ is preferably a hydrogen atom, a substituted or unsubstituted alkyl group having 1 to 18 carbon atoms, or a substituted or unsubstituted aryl group having 6 to 24 carbon atoms.

When u is 2, $Y^2$ represents a divalent substituent. Examples of the divalent substituent include the same examples as the aforementioned divalent substituent -L-. $Y_2$ is preferably a substituted or unsubstituted divalent alkyl group, a substituted or unsubstituted divalent alkenyl group, a substituted or unsubstituted divalent aryl group, —$CH_2CH(OH)CH_2$—O—$Y_{11}$—$OCH_2CH(OH)CH_2$, —CO—$Y_{12}$—CO—, —CO—NH—$Y_{13}$—NH—CO—, or —$(CH_2)_rCO_2$—$Y_{14}$—OCO—$(CH_2)_r$.

Herein, t is 1, 2 or 3;

$Y_{11}$ represents a substituted or unsubstituted alkylene group, phenylene group, or -phenylene-M-phenylene- (wherein, M represents —O—, —S—, —SO$_2$—, —CH$_2$— or —C(CH$_3$)$_2$—);

$Y_{12}$ represents a substituted or unsubstituted divalent alkyl group, a substituted or unsubstituted divalent alkenyl group or a substituted or unsubstituted divalent aryl group;

$Y_{13}$ represents a substituted or unsubstituted divalent alkyl group or a substituted or unsubstituted divalent aryl group; and $Y_{14}$ represents a substituted or unsubstituted divalent alkyl group or a substituted or unsubstituted divalent aryl group.

That is, when u is 2, $Y_2$ is preferably a substituted or unsubstituted divalent alkyl group having 1 to 18 carbon atoms, a substituted or unsubstituted divalent aryl group having 6 to 24 carbon atoms, —CH$_2$CH(OH)CH$_2$—O—CH$_2$—OCH$_2$CH(OH)CH$_2$—, —CH$_2$CH(OH)CH$_2$—O—C(CH$_3$)$_2$—OC$_8$H$_{16}$—, or —(CH$_2$)$_2$—CO$_2$—C$_2$H$_4$—OCO—(CH$_2$)$_2$—.

Typical examples of the compound represented by formula (III) include 2-(4-butoxy-2-hydroxyphenyl)-4,6-di(4-butoxyphenyl)-1,3,5-triazine, 2-(4-butoxy-2-hydroxyphenyl)-4,6-di(2,4-dibutoxyphenyl)-1,3,5-triazine, 2,4-di(4-butoxy-2-hydroxyphenyl)-6-(4-butoxyphenyl)-1,3,5-triazine, 2,4-di(4-butoxy-2-hydroxyphenyl)-6-(2,4-dibutoxyphenyl)-1,3,5-triazine, 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris(2-hydroxy-4-(3-butoxy-2-hydroxypropoxy)phenyl)-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxy-propyloxy]phenyl}-4,6-bis(2,4-dimethylphenyl)-1,3,5-triazine and 2-(2-hydroxy-4-(2-ethylhexyl)oxy)phenyl-4,6-di(4-phenyl)phenyl-1,3,5-triazine.

The benzophenone-based compound is preferably a compound having an effective absorption wavelength of approximately 270 to 380 nm that is represented by formula (IVa) or (IVb).

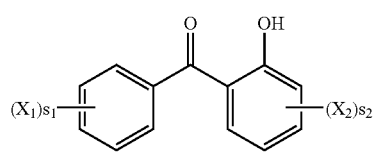

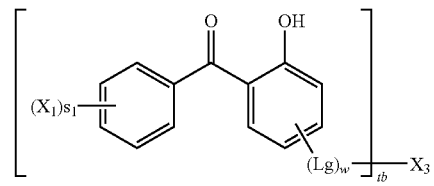

(In formula (IVa), $X_1$ and $X_2$ each independently represent a hydrogen atom, a halogen atom, a hydroxyl group, a substituted or unsubstituted alkyl group, a substituted or unsubstituted phenyl group, a substituted or unsubstituted alkoxy group, a substituted or unsubstituted alkylsulfonyl group, a substituted or unsubstituted arylsulfonyl group, a sulfonic acid group, a substituted or unsubstituted alkyloxycarbonyl group, a substituted or unsubstituted aryloxycarbonyl group or a substituted or unsubstituted amino group; and s1 and s2 each independently represent an integer of 1 to 3.)

(In formula (IVb), $X_1$ represents a hydrogen atom, a halogen atom, a hydroxyl group, a substituted or unsubstituted alkyl group, a substituted or unsubstituted phenyl group, a substituted or unsubstituted alkoxy group, a substituted or unsubstituted alkylsulfonyl group, a substituted or unsubstituted arylsulfonyl group, a sulfonic acid group, a substituted or unsubstituted alkyloxycarbonyl group, a substituted or unsubstituted aryloxycarbonyl group or a substituted or unsubstituted amino group; s1 represents an integer of 1 to 3;

Lg represents a divalent substituent or a single bond; w represents 0 or 1;

tb represents 1 or 2; and when tb is 1, $X_3$ represents a hydrogen atom, a halogen atom, a hydroxyl group, a substituted or unsubstituted alkyl group, a substituted or unsubstituted phenyl group, a substituted or unsubstituted alkoxy group, a substituted or unsubstituted alkylsulfonyl group, a substituted or unsubstituted arylsulfonyl group, a sulfonic acid group, a substituted or unsubstituted alkyloxycarbonyl group, a substituted or unsubstituted aryloxycarbonyl group or a substituted or unsubstituted amino group; and when tb is 2, $X_3$ represents a divalent substituent.

(Formula (IVa))

$X_1$ and $X_2$ each independently represent a hydrogen atom, a halogen atom, a hydroxyl group, a substituted or unsubstituted alkyl group, a substituted or unsubstituted phenyl group, a substituted or unsubstituted alkoxy group, a substituted or unsubstituted alkylsulfonyl group, a substituted or unsubstituted arylsulfonyl group, a sulfonic acid group, a substituted or unsubstituted alkyloxycarbonyl group, a substituted or unsubstituted aryloxycarbonyl group or a substituted or unsubstituted amino group. $X_1$ and $X_2$ each are preferably a hydrogen atom, a chlorine atom, a hydroxyl group, a substituted or unsubstituted alkyl group having 1 to 18 carbon atoms, a substituted or unsubstituted aryl group having 6 to 24 carbon atoms, a substituted or unsubstituted alkoxy group having 1 to 18 carbon atoms, a substituted or unsubstituted alkyloxycarbonyl group having 2 to 18 carbon atoms, a substituted or unsubstituted aryloxycarbonyl group having 7 to 24 carbon atoms, a sulfonic acid group or a substituted or unsubstituted amino group having 1 to 16 carbon atoms; and particularly preferably a hydrogen atom, a hydroxyl group, a substituted or unsubstituted alkoxy group having 1 to 18 carbon atoms, a sulfonic acid group or a substituted or unsubstituted amino group having 1 to 16 carbon atoms.

(Formula (IVb))

tb is 1 or 2, w is 0 or 1, and s1 is an integer of 1 to 3.

The substituent $X_1$ represents a hydrogen atom, a halogen atom, a hydroxyl group, a substituted or unsubstituted alkyl group, a substituted or unsubstituted phenyl group, a substituted or unsubstituted alkoxy group, a substituted or unsubstituted alkylsulfonyl group, a substituted or unsubstituted arylsulfonyl group, a sulfonic acid group, a substituted or unsubstituted alkyloxycarbonyl group, a substituted or unsubstituted aryloxycarbonyl group or a substituted or unsubstituted amino group.

$X_1$ is preferably a hydrogen atom, a chlorine atom, a hydroxyl group, a substituted or unsubstituted alkyl group having 1 to 18 carbon atoms, a substituted or unsubstituted aryl group having 6 to 24 carbon atoms, a substituted or unsubstituted alkoxy group having 1 to 18 carbon atoms, a substituted or unsubstituted alkyloxycarbonyl group having 2 to 18 carbon atoms, a substituted or unsubstituted aryloxycarbonyl group having 7 to 24 carbon atoms, a sulfonic acid group or a substituted or unsubstituted amino group having 1 to 16 carbon atoms; and particularly preferably a hydrogen atom, a hydroxyl group, a substituted or unsubstituted alkoxy group having 1 to 18 carbon atoms, a sulfonic acid group or a substituted or unsubstituted amino group having 1 to 16 carbon atoms.

-Lg- represents a divalent linking group or a single bond. w represents an integer of 0 or 1. The case where w is 0 (zero) means that $X_3$ directly bonds with the benzene ring without involving Lg, that is -Lg- represents a single bond.

The divalent linking group -Lg- is explained. The divalent linking group Lg is a divalent substituent represented by formula (c).

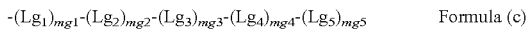

In formula (c), mg1, mg2, mg3, mg4 and mg5 each represent an integer of 0 to 2.

$Lg_1$, $Lg_2$, $Lg_3$, $Lg_4$ and $Lg_5$ each independently represent —CO—, —O—, —$SO_2$—, —SO—, —$NRg_L$-, a substituted or unsubstituted divalent alkyl group, a substituted or unsubstituted divalent alkenyl group, or a substituted or unsubstituted divalent aryl group. $Rg_L$ represents a hydrogen atom, a substituted or unsubstituted alkyl group or a substituted or unsubstituted aryl group.

Examples of $Rg_L$, include a hydrogen atom, a methyl group, an ethyl group, a propyl group, a hexyl group, an octyl group, a phenyl group, and a naphthyl group. The group may be substituted with one or more monovalent substituents at any position of the alkyl or aryl groups. The monovalent substituent is, for example, a monovalent substituent described above. $Rg_L$, is preferably a substituted or unsubstituted alkyl group having 3 to 20 carbon atoms or a substituted or unsubstituted aryl group having 6 to 14 carbon atoms; and more preferably a substituted or unsubstituted alkyl group having 6 to 12 carbon atoms or a substituted or unsubstituted aryl group having 6 to 10 carbon atoms.

That is, preferred examples of the divalent substituent -Lg- include —O—, —O—CO—$C_2H_4$—CO—O—, —O—$C_4H_8$—O—, —O—CO—$C_3H_6$—, —NH—CO—$C_3H_6$—CO—NH—, —NH—CO—$C_4H_8$—, —$CH_2$—, —$C_2H_4$—, —$C_3H_6$—, —$C_4H_8$—, —$C_5H_{10}$—, —$C_8H_{16}$—, —$C_4H_8$—CO—O—, —$C_6H_4$—$C_6H_4$—, and —NH—$SO_2$—$C_3H_6$—.

When tb is 1, $X_3$ represents a hydrogen atom, a halogen atom, a hydroxyl group, a substituted or unsubstituted phenyl group, a substituted or unsubstituted alkyl group, a substituted or unsubstituted alkoxy group, a substituted or unsubstituted alkylsulfonyl group, a substituted or unsubstituted arylsulfonyl group, a sulfonic acid group, a substituted or unsubstituted alkyloxycarbonyl group, a substituted or unsubstituted aryloxycarbonyl group or a substituted or unsubstituted amino group.

When tb is 1, $X_3$ is preferably a hydrogen atom, a hydroxyl group, a chlorine atom, a substituted or unsubstituted alkyl group having 1 to 18 carbon atoms, a substituted or unsubstituted aryl group having 6 to 24 carbon atoms, a substituted or unsubstituted alkoxy group having 1 to 18 carbon atoms, a substituted or unsubstituted alkyloxycarbonyl group having 2 to 18 carbon atoms, a substituted or unsubstituted aryloxycarbonyl group having 7 to 24 carbon atoms, a sulfonic acid group, or a substituted or unsubstituted amino group having 1 to 16 carbon atoms.

$X_3$ is particularly preferably a hydrogen atom, a hydroxyl group, a substituted or unsubstituted alkoxy group having 1 to 18 carbon atoms, a sulfonic acid group, or a substituted or unsubstituted amino group having 1 to 16 carbon atoms.

When tb is 2, $X_3$ represents a divalent substituent.

When tb is 2, examples of $X_3$ include the same examples as the above-described divalent substituent -L-. When tb is 2, $X_3$ is preferably —$CH_2$—, —$C_4H_8$—, —O—$C_4H_8$—O—, —O—CO—$C_2$—$H_4$—CO—O—, or —NH—CO—$C_3H_6$—CO—NH—.

In formula (IVb), tb is particularly preferably 1.

That is, the component of formula (IVb) is preferable combined as follows.

Specifically, when tb is 1, a preferable combination is that $X_1$ is a hydrogen atom, a hydroxyl group, a substituted or unsubstituted alkoxy group having 1 to 18 carbon atoms, a sulfonic acid group, or a substituted or unsubstituted amino group having 1 to 16 carbon atoms;

Lg is —O—, —O—$C_4H_8$—O—, —O—CO—$C_3H_6$—, —NH—CO—$C_3H_6$—CO—NH—, —NH—CO—$C_4H_8$—, —$CH_2$—, —$C_2H_4$—, —$C_3H_6$—, —$C_4H_8$—, —$C_5H_{10}$—, —$C_8H_{16}$—, —$C_4H_8$—CO—O—, —$C_6H_4$—$C_6H_4$—, —NH—$SO_2$—$C_3H_6$—, or a single bond; and $X_3$ is a hydrogen atom, a hydroxyl group, a chlorine atom, a substituted or unsubstituted alkyl group having 1 to 18 carbon atoms, a substituted or unsubstituted aryl group having 6 to 24 carbon atoms, a substituted or unsubstituted alkoxy group having 1 to 18 carbon atoms, a substituted or unsubstituted alkyloxycarbonyl group having 2 to 18 carbon atoms, a substituted or unsubstituted aryloxycarbonyl group having 7 to 24 carbon atoms, a sulfonic acid group, or a substituted or unsubstituted amino group having 1 to 16 carbon atoms.

When tb is 2, a preferable combination is that $X_1$ is a hydrogen atom, a hydroxyl group, a substituted or unsubstituted alkoxy group having 1 to 18 carbon atoms, a sulfonic acid group, or a substituted or unsubstituted amino group having 1 to 16 carbon atoms;

Lg is —O—, —O—CO—$C_2H_4$—CO—O—, —O—$C_4H_8$—O—, —O—CO—$C_3H_6$—, —NH—CO—$C_3$—$H_6$—CO—NH—, —NH—CO—$C_4H_8$—, —$CH_2$—, —$C_2H_1$—, —$C_3H_6$—, —$C_4H_8$—, —$C_5H_{10}$—, —$C_8H_{16}$—, —$C_4H_8$—CO—O—, —$C_6H_4$—$C_6H_4$—, —NH—$SO_2$—$C_3H_6$—, or a single bond; and $X_3$ is —$CH_2$—, —$C_4H_8$—, —O—$C_4H_8$—O—, —O—CO—$C_2H_4$—CO—O—, or —NH—CO—$C_3H_6$—CO—NH—.

Typical examples of the benzophenone-based compound include 2,4-dihydroxybenzophenone, 2-hydroxy-4-methoxybenzophenone, 2-hydroxy-4-octyloxybenzophenone, 2-hydroxy-4-decyloxybenzophenone, 2-hydroxy-4-dodecyloxybenzophenone, 2-hydroxy-4-benzyloxybenzophenone, 2-hydroxy-4-(2-hydroxy-3-methacryloxypropoxy)benzophenone, 2-hydroxy-4-methoxy-5-sulfobenzophenone, 2-hydroxy-4-methoxy-5-sulfobenzophenone trihydrate, 2-hydroxy-4-methoxy-2'-carboxybenzophenone, 2-hydroxy-4-octadecyloxybenzophenone, 2-hydroxy-4-diethylamino-2'-hexyloxycarbonylbenzophenone, 2,2'-dihydroxy-4-methoxybenzophenone, 2,2',4,4'-tetrahydroxybenzophenone, 2,2'-dihydroxy-4,4'-dimethoxybenzophenone, and 1,4-bis(4-benzyloxy-3-hydroxyphenoxy)butane.

The salicylic acid-based compound above is preferably a compound having an effective absorption wavelength of approximately 290 to 330 nm, and typical examples thereof include phenyl salicylate, 4-t-butylphenyl salicylate, 4-octylphenyl salicylate, dibenzoylresorcinol, bis(4-t-butylbenzoyl)resorcinol, benzylresorcinol, 2,4-di-t-butylphenyl 3,5-di-t-butyl-4-hydroxysalicylate, and hexadecyl 3,5-di-t-butyl-4-hydroxysalicylate.

The acrylate-based compound above is preferably a compound having an effective absorption wavelength of approximately 270 to 350 nm, and typical examples thereof include 2-ethylhexyl 2-cyano-3,3-diphenylacrylate, ethyl 2-cyano-3,3-diphenylacrylate, isooctyl 2-cyano-3,3-diphenylacrylate, hexadecyl 2-cyano-3-(4-methylphenyl)acrylate, methyl 2-cyano-3-methyl-3-(4-methoxyphenyl)cinnamate, butyl 2-cyano-3-methyl-3-(4-methoxyphenyl)cinnamate, methyl 2-carbomethoxy-3-(4-methoxyphenyl)cinnamate 2-cyano-3-(4-methylphenyl)acrylate salt, 1,3-bis(2'-cyano-3,3'-diphenylacryloyl)oxy)-2,2-bis(((2'-cyano-3,3'-diphenylacryloyl)oxy)methyl)propane, and N-(2-carbomethoxy-2-cyanovinyl)-2-methylindoline.

The oxalic diamide-based compound above is preferably a compound having an effective absorption wavelength of approximately 250 to 350 nm, and typical examples thereof include 4,4'-dioctyloxyoxanilide, 2,2'-dioctyloxy-5,5'-di-t-butyloxanilide, 2,2'-didodecyloxy-5,5'-di-t-butyloxanilide, 2-ethoxy-2'-ethyloxanilide, N,N'-bis(3-dimethylaminopropyl)oxamide, 2-ethoxy-5-t-butyl-2'-ethyloxanilide, and 2-ethoxy-2'-ethyl-5,4'-di-t-butyloxanilide.

The ultraviolet absorbent composition of the present invention may further contain a light stabilizer, or an antioxidant.

Preferable examples of the light stabilizer and the antioxidant include compounds described in JP-A-2004-117997. Specifically, compounds described on page 29, middle paragraph Nos. [0071] to [0111] of JP-A-2004-117997 are preferable. Especially, compounds represented by formula (TS-I), (TS-II), (TS-IV), or (TS-V) described on the paragraph No. [0072] are preferable.

The content of the compound represented by any one of formulae (2) to (5), in the polymer material according to the present invention, may vary according to the application and the usage of the polymer material and thus cannot be defined specifically, but can be determined easily by the person skilled in the art after some tests. It is preferably 0.001 to 10 mass %, more preferably 0.01 to 5 mass %, with respect to the total amount of the polymer material. The content of the ultraviolet absorbent other than the compound represented by any one of formulae (2) to (5) above can be determined properly according to the application of the present invention.

Although practically sufficient ultraviolet-shielding effect is obtained only with the ultraviolet absorbent in the present invention, a white pigment which has higher hiding power such as titanium oxide may be used for assurance. In addition, a trace (0.05 mass % or less) amount of colorant may be used additionally, if the appearance or the color tone is of a problem or as needed. Alternatively, a fluorescent brightener may be used additionally for applications demanding transparency or whiteness. Examples of the fluorescent brighteners include commercialized products, the compounds described in JP-A-2002-53824, and the like.

Hereinafter, the polymer substance that can be used in the polymer material of the present invention will be described. An acrylic acid-based polymer, a polyester, a polycarbonate, or the blend thereof is preferably used as the polymer substance. Hereinafter, each of the polymers will be described in detail.

(Acrylic Acid-Based Polymer)

The acrylic acid-based polymer, as used herein, is a homopolymer or a copolymer obtained by polymerization of a compound represented by formula A1 as the monomer component.

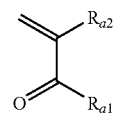

(Formula A1)

(In formula $A_1$, $R_{a1}$ represents a hydroxyl group, a substituted or unsubstituted alkoxy group, a substituted or unsubstituted amino group, a substituted or unsubstituted alkyl group, a substituted or unsubstituted aryl group, or a substituted or unsubstituted heterocyclic group; $R_{a2}$ represents a hydrogen atom, a methyl group, or an alkyl group having 2 or more carbon atoms.)

The formula A1 will be described in detail.

In formula A1, $R_{a1}$ represents a hydroxyl group, a substituted or unsubstituted alkoxy group, a substituted or unsubstituted aryloxy group, a substituted or unsubstituted amino group, a substituted or unsubstituted alkyl group, a substituted or unsubstituted aryl group, or a substituted or unsubstituted heterocyclic group. Among these, $R_{a1}$ is preferably a substituted or unsubstituted alkoxy group, or a substituted or unsubstituted aryloxy group; and particularly preferably a substituted or unsubstituted alkoxy group having 1 to 18 carbon atoms, or a substituted or unsubstituted aryloxy group having 6 to 24 carbon atoms.

$R_{a2}$ represents a hydrogen atom, a methyl group, or an alkyl group having 2 or more carbon atoms. Among these, $R_{a2}$ is preferably a hydrogen atom or a methyl group.

Thus, in preferable combination of the substituents of formula $A_1$, $R_{a1}$ represents a substituted or unsubstituted alkoxy group having 1 to 18 carbon atoms or a substituted or unsubstituted aryloxy group having 6 to 24 carbon atoms, and $R_{a2}$ represents a hydrogen atom or a methyl group.

Typical examples of the compound represented by formula A1 include the followings:

acrylate derivatives such as methyl acrylate, ethyl acrylate, (n- or i-)propyl acrylate, (n-, i-, sec- or t-)butyl acrylate, amyl acrylate, 2-ethylhexyl acrylate, dodecyl acrylate, chloroethyl acrylate, 2-hydroxyethyl acrylate, 2-hydroxypropyl acrylate, 2-hydroxypentyl acrylate, cyclohexyl acrylate, allyl acrylate, trimethylolpropane monoacrylate, pentaerythritol monoacrylate, benzyl acrylate, methoxybenzyl acrylate, chlorobenzyl acrylate, hydroxybenzyl acrylate, hydroxyphenethyl acrylate, dihydroxyphenethyl acrylate, furfuryl acrylate, tetrahydrofurfuryl acrylate, phenyl acrylate, hydroxyphenyl acrylate, chlorophenyl acrylate, sulfamoylphenyl acrylate, and 2-(hydroxyphenylcarbonyloxy) ethyl acrylate;

methacrylate derivatives such as methyl methacrylate, ethyl methacrylate, (n- or i-) propyl methacrylate, (n-, i-, sec- or t-)butyl methacrylate, amyl methacrylate, 2-ethylhexyl methacrylate, dodecyl methacrylate, chloroethyl methacrylate, 2-hydroxyethyl methacrylate, 2-hydroxypropyl methacrylate, 2-hydroxypentyl methacrylate, cyclohexyl methacrylate, allyl methacrylate, trimethylolpropane monomethacrylate, pentaerythritol monomethacrylate, benzyl methacrylate, methoxybenzyl methacrylate, chlorobenzyl methacrylate, hydroxybenzyl methacrylate, hydroxyphenethyl methacrylate, dihydroxyphenethyl methacrylate, furfuryl methacrylate, tetrahydrofurfuryl methacrylate, phenyl methacrylate, hydroxyphenyl methacrylate, chlorophenyl methacrylate, sulfamoylphenyl methacrylate, and 2-(hydroxyphenylcarbonyloxy)ethyl methacrylate;

acrylamide derivatives such as acrylamide, N-methylacrylamide, N-ethylacrylamide, N-propylacrylamide, N-butylacrylamide, N-benzylacrylamide, N-hydroxyethylacrylamide, N-phenylacrylamide, N-tolylacrylamide, N-(hydroxyphenyl)acrylamide, N-(sulfamoylphenyl)acrylamide, N-(phenylsulfonyl)acrylamide, N-(tolylsulfonyl)acrylamide, N,N-dimethylacrylamide, N-methyl-N-phenylacrylamide, and N-hydroxyethyl-N-methylacrylamide; and methacrylamide derivatives such as methacrylamide, N-methylmethacrylamide, N-ethylmethacrylamide, N-propylmethacrylamide, N-butylmethacrylamide, N-benzylmethacrylamide, N-hydroxyethylmethacrylamide, N-phenylmethacrylamide, N-tolylmethacrylamide, N-(hydroxyphenyl)methacrylamide, N-(sulfamoylphenyl)methacrylamide, N-(phenylsulfonyl)methacrylamide, N-(tolylsulfonyl)methacrylamide, N,N-dimethylmethacrylamide, N-methyl-N-phenylmethacrylamide, and N-hydroxyethyl-N-methylmethacrylamide.

The acrylic acid-based polymer is preferably a single-component homopolymer obtained by polymerization of the monomer represented by formula A1 above or a two-, three- or four-component, more preferably two- or three-component, copolymer prepared by polymerization using the monomer represented by formula A1 above at a molar ratio of 10% to 90%, preferably 20% to 80% and also other monomer components or the other monomer components represented by formula A1 above. Examples of the other monomer components include a substituted or unsubstituted styrene derivative, and acrylonitrile.

The acrylic acid-based polymer is preferably a homopolymer containing an acrylate or a methacrylate having 4 to 24 carbon atoms as the monomer component or a two- or three-component copolymer containing an acrylate or a methacrylate as the monomer component at a molar ratio of 10% to 90%.

(Polyester)

Hereinafter, the polyester will be described.

The polyester that can be used in the present invention contains the following dicarboxylic acid, the acid halide thereof or the following polyvalent carboxylic acid; and a diol as monomer components.

Examples of the dicarboxylic acid or the acid halides thereof include aliphatic, alicyclic dicarboxylic acids such as adipic acid, superic acid, azelaic acid, sebacic acid, dodecanedioic acid, oxalic acid, malonic acid, succinic acid, glutaric acid, ethylsuccinic acid, pimelic acid, maleic acid, fumaric acid, itaconic acid, citraconic acid, mesaconic acid, 2-methylsuccinic acid, 2-methyladipic acid, 3-methyladipic acid, 3-methylpentanedioic acid, 2-methyloctanedioic acid, 3,8-dimethyldecanedioic acid, 3,7-dimethyldecanedioic acid, dimer acid, hydrogenated dimer acids, 1,2- or 1,3-cyclopentanedicarboxylic acids, and 1,2-, 1,3- or 1,4-cyclohexanedicarboxylic acids; and aromatic dicarboxylic acids such as phthalic acid, isophthalic acid, terephthalic acid, 1,4-naphthalenedicarboxylic acid, 2,5-naphthalenedicarboxylic acid, 2,6-naphthalenedicarboxylic acid, naphthalic acid, biphenyldicarboxylic acid, 2-methylisophthalic acid, 3-methylphthalic acid, 2-methylterephthalic acid, 2,4,5,6-tetramethylisophthalic acid, 3,4,5,6-tetramethylphthalic acid, 2-chloroterephthalic acid, 2-methylterephthalic acid, 5-methylisophthalic acid, 5-sodium sulfoisophthalic acid, 2,6-naphthalenedicarboxylic acid, hexahydroterephthalic acid, hexahydroisophthalic acid, 3-chloroisophthalic acid, 3-methoxyisophthalic acid, 2-fluoroisophthalic acid, 3-fluorophthalic acid, 2-fluoroterephthalic acid, 2,4,5,6-tetrafluoroisophthalic acid, 3,4,5,6-tetrafluorophthalic acid, 4,4'-oxybisbenzoic acid, 3,3'-oxybisbenzoic acid, 3,4'-oxybisbenzoic acid, 2,4'-oxybisbenzoic acid, 3,4'-oxybisbenzoic acid, 2,3'-oxybisbenzoic acid, 4,4'-oxybisoctafluorobenzoic acid, 3,3'-oxybisoctafluorobenzoic acid, 1,4-naphthalenedicarboxylic acid, 2,6-naphthalenedicarboxylic acid, 4,4'-biphenyldicarboxylic acid, 4,4'-diphenylethercarboxylic acid; and the like.

Examples of the polyvalent carboxylic acids other than the dicarboxylic acids include ethanetricarboxylic acid, propanetricarboxylic acid, butanetetracarboxylic acid, pyromellitic acid, trimellitic acid, trimesic acid, and 3,4,3',4'-biphenyltetracarboxylic acid.

With respect to the polyester in the present invention, among these dicarboxylic acids and polyvalent carboxylic acid components, use of adipic acid, malonic acid, succinic acid, terephthalic acid, isophthalic acid, phthalic acid, 1,4-naphthalenedicarboxylic acid, 2,5-naphthalenedicarboxylic acid, 2,6-naphthalenedicarboxylic acid or trimellitic acid is preferable; and use of terephthalic acid, isophthalic acid, 1,4-naphthalenedicarboxylic acid, 2,5-naphthalenedicarboxylic acid or 2,6-naphthalenedicarboxylic acid is particularly preferable.

Examples of the diols include aliphatic glycols such as ethylene glycol, 1,2-propylene glycol, 1,3-propylene glycol, diethylene glycol, triethylene glycol, 1,2-butylene glycol, 1,3-butylene glycol, 2,3-butylene glycol, 1,4-butylene glycol, 1,5-pentanediol, neopentylglycol, 1,6-hexanediol, 1,2-cyclohexanediol, 1,3-cyclohexanediol, 1,4-cyclohexanediol, 1,2-cyclohexanedimethanol, 1,3-cyclohexanedimethanol, 1,4-cyclohexanedimethanol, 1,4-cyclohexanediethanol, 1,10-decamethylene glycol, 1,12-dodecanediol, polyethylene glycol, polytrimethylene glycol, and polytetramethylene glycol; aromatic glycols such as hydroquinone, 4,4'-dihydroxybisphenol, 1,4-bis(β-hydroxyethoxy)benzene, 1,4-bis(β-hydroxyethoxyphenyl)sulfone, bis(p-hydroxyphenyl)ether, bis(p-hydroxyphenyl)sulfone, bis(p-hydroxyphenyl)methane, 1,2-bis(p-hydroxyphenyl)ethane, bisphenol A, bisphenol C, 2,5-naphthalenediol, and ethyleneoxide adducts of these glycols; and the like.

With respect to the polyester that can be used in the present invention, among these diol components, use of ethylene glycol, 1,3-propylene glycol, diethylene glycol, neopentylglycol, hydroquinone, 4,4'-dihydroxybisphenol or bisphenol A is preferable; and use of ethylene glycol or 4,4'-dihydroxybisphenol is particularly preferable.

Specifically, preferable combinations of monomers and preferable polymers in the polyester that can be used in the present invention include polyethylene terephthalate prepared by using terephthalic acid as the dicarboxylic acid component and ethylene glycol as the diol component, polybutylene terephthalate prepared by using terephthalic acid as the dicarboxylic acid component and 1,4-butylene glycol as the diol component, and polyethylene naphthalate prepared by using 2,6-naphthalenedicarboxylic acid as the dicarboxylic acid component and ethylene glycol as the diol component.

(Polycarbonate)

The polycarbonate that can be used in the present invention is prepared from the following polyvalent phenols and the following carbonates such as bisalkyl carbonate, bisaryl carbonate or phosgene.

Examples of the polyvalent phenols include hydroquinone, resorcin, 4,4'-dihydroxydiphenyl, bis(4-hydroxyphenyl)methane, 1,1-bis(4-hydroxyphenyl)ethane, 1,1-bis(4-hydroxyphenyl)-1-phenylethane, bisphenol A, bisphenol C, bisphenol E, bisphenol F, bisphenol M, bisphenol P, bisphenol S, bisphenol Z, 2,2-bis(3-methyl-4-hydroxyphenyl)propane, 1,1-bis(4-hydroxyphenyl)cyclohexane, 2,2-bis(3-phenyl-4-hydroxyphenyl)propane, 2,2-bis(3-isopropyl-4-hydroxyphenyl)propane, 2,2-bis(4-hydroxyphenyl)butane, 2,2-bis(3,5-dimethyl-4-hydroxyphenyl)propane, 2,2-bis(3,5-dibromo-4-hydroxyphenyl)propane, 4,4'-dihydroxydiphenylsulfone, 4,4'-dihydroxydiphenylsulfoxide, 4,4'-dihydroxydiphenylsulfide, 3,3'-dimethyl-4,4'-dihydroxydiphenylsulfide, and 4,4'-dihydroxydiphenyloxide.

With respect to the polycarbonate that can be used in the present invention, among these polyvalent phenol components, use of hydroquinone, resorcin, 4,4'-dihydroxydiphenyl or bisphenol A is preferable.

Examples of the carbonates include phosgene, diphenyl carbonate, bis(chlorophenyl)carbonate, dinaphthyl carbonate, bis(diphenyl)carbonate, dimethyl carbonate, diethyl carbonate, and dibutyl carbonate.

With respect to the polycarbonate that can be used in the present invention, among these carbonate components, use of phosgene, bis(diphenyl)carbonate, dimethyl carbonate, or diethyl carbonate is preferable.

Specifically, a preferable combination of monomers, i.e., a preferable polymer in the polycarbonate that can be used in the present invention is bisphenol A carbonate, which is prepared by using bisphenol A as the polyvalent phenol component and phosgene as the carbonate component.

Among the polymers above, polymethyl acrylate, polymethyl methacrylate, polyethylene terephthalate, polyethylene naphthalate, polybutylene terephthalate and polycarbonate are particularly preferable. Unexpectedly to the person skilled in the art, use of one of the preferable polymer substances resulted in drastic improvement in light fastness of the ultraviolet absorbent, compared to the ultraviolet absorbent prepared with a polymer substance other than those above.

The polymer substance for use in the present invention is preferably a thermoplastic resin.

The polymer substance for use in the present invention preferably has a transmittance of 80% or more. The transmittance in the present invention is the total light transmittance as determined according to the method described in the Chemical Society of Japan Ed., "Experimental Chemistry Lecture 29—Polymer materials," 4th Ed., (Maruzen, 1992) p. 225 to 232.

The glass transition point (Tg) of the polymer substance for use in the present invention is preferably −80° C. or higher and 200° C. or lower, still more preferably −30° C. or higher and 180° C. or lower. In particular, a polyacrylate, a polycarbonate and a polyethylene terephthalate are preferable.

The polymer material prepared by using a polymer substance having a Tg in the range above gives a polymer material favorably in flexibility and hardness. When a polyacrylate, polycarbonate or polyethylene terephthalate is used, it leads to improvement in operational efficiency; and when the ultraviolet absorbent in the present invention is used, it leads to improvement in the light fastness of the ultraviolet absorbent itself.

The polymer material according to the present invention may contain any additives such as antioxidant, photostabilizer, processing stabilizer, antidegradant, and compatibilizer, as needed in addition to the polymer substance above and the ultraviolet light inhibitor.

The polymer material according to the present invention contains the polymer substance above. The polymer material according to the present invention may be made only of the above-described polymer substance, or may be formed by using the polymer substance dissolved in a solvent.

When the polyethylene terephthalate is used as the polymer substance, the polymer material according to the present invention is preferably produced by melt-kneading of the polyethylene terephthalate and the ultraviolet absorbent at a temperature of 200° C. or higher. (Polymer materials prepared by the melt-kneading polyethylene terephthalate at the temperature or less possibly may give polymer materials containing the ultraviolet absorbent unevenly dispersed in the spot-like pattern. The content of the ultraviolet absorbent in the polymer material according to the present invention is preferably 0.1 mass % to 50 mass %, more preferably 0.1 mass % to 25 mass %, and particularly preferably 0.4 mass % to 10 mass %, with respect to 100 mass % of the polyethylene terephthalate. A content of not more than 0.1 mass % may result in production of a polymer material that does not absorb the light in the ultraviolet region completely, because of insufficiency of the ultraviolet absorbent added.

The compound having the structure defined in the present invention, which is superior in solubility, gives a polymer material easily, as it is dissolved in a various solvent with a polymer and the solution coated. In preparation of the polymer material, a plasticizer may not be added. In addition, a polymer material prepared by solvent coating or polymer kneading has an advantage that it is superior in light fastness, compared to the polymer material prepared by using a plasticizer.

The compound represented by any one of formulae (2) to (5) mostly have a molecular weight of 1000 or less, and thus, the idea of using such a compound as it is melted under an environment at high temperature for prolonged period, for example during PET kneading, which may lead to volatilization and decomposition, was not easily conceived by the person skilled in the art.

When the polyethylene terephthalate is used, the compound represented by any one of formulae (3) to (5) above is preferably used, because it is resistant to volatilization and decomposition. Use of the compound represented by formula (4) or (5) is particularly preferable, and the compound represented by formula (5) is still more preferable.

When the an acrylate or the polycarbonate is used as the polymer substance, the polymer material according to the present invention is preferably prepared by dissolving the acrylate and the ultraviolet absorbent in a solvent having a boiling point of 200° C. or lower and coating the resulting solution on a base plate. If a solvent having a boiling point of 200° C. or higher is used, it is needed to volatilize the solvent at high temperature, which may make the processing step more complicated. The content of the ultraviolet absorbent in the polymer material according to the present invention, is preferably 0.1 mass % to 50 mass %, more preferably 0.1 mass % to 25 mass %, and particularly more preferably 0.4 mass % to 10 mass %, with respect to 100 mass % of the acrylate or the polycarbonate. When the added amount is 0.1 mass % or less, polymer materials absorbing the light in the entire ultraviolet region may not be produced, because of insufficiency of the ultraviolet absorbent added.

When the acrylate or polycarbonate is used as the polymer substance for coating, use of the compound represented by any one of formulae (3) to (5) above is preferable from the viewpoint of solubility in solvent and compatibility with polymer. It is particularly preferable to use the compound represented by formula (4) or (5), still more preferable to use the compound represented by formula (5).

The polymer material according to the present invention is applicable to any application where synthetic resin is used, and particularly favorably to applications where there is possibility of exposure to light such as sunlight or ultraviolet light. Specific examples thereof include glass alternatives and their surface-coating agent; coating agents for the window glass, lighting glass and light-protecting glass such as of house, facility, and vehicle; interior and exterior materials such as of house, facility and vehicle, paints for the interior and exterior materials; materials for ultraviolet-emission sources such as fluorescent lamp and mercury lamp; materials for precision machines and electric and electronic devices; materials for shielding electromagnetic and other waves emitted from various displays; containers and packaging materials such as of food, beverage, and medicine; discoloration inhibitors for agricultural and industrial sheet or film, print, colored products, dyes and pigments; cosmetics such as antisunburn cream, shampoo, rinse, and hair dressing; apparel fiber products such as sport wear, stockings and cap and the fibers; home interior products such as curtain, carpet and wall paper; medical devices such as plastic lens, contact lens and artificial eye; optical materials such as optical filter, prism, mirror, and photographic material; stationery products such as tape and ink; display plates and devices and the surface-coating agents thereof, and the like. Alternatively, the polymer material according to the present invention may be used in cosmetic applications.

The shape of the polymer material according to the present invention may be flat film, powder, spherical particle, crushed particle, bulky continuous particle, fiber, solenoid, hollow fiber, granule, plate, porous particle, or the other.

The polymer material according to the present invention, which contains the ultraviolet absorbing compound represented by any one of formula (2) to (5), is superior in light resistance (ultraviolet fastness), causing no precipitation or bleed out of the ultraviolet absorbent during long-term use. In addition, the polymer material according to the present invention, which has superior long-wavelength ultraviolet absorption capacity, can be used as an ultraviolet-absorbing filter or container, for protection, for example, of an ultraviolet-sensitive compound therein. It is possible to obtain a molded article (such as container) of the polymer material according to the present invention, for example, by molding the polymer substance by any molding method such as extrusion molding or injection molding. It is also possible to prepare a molded article coated with an ultraviolet-absorbing film made of the polymer material according to the present invention, by coating and drying a solution of the polymer substance on a separately prepared molded article.

When the polymer material according to the present invention is used as an ultraviolet-absorbing filter or film, the polymer substance is preferably transparent. Examples of the transparent polymer materials include polycarbonate, polyesters (e.g., polyethylene terephthalate, polyethylene naphthalate, polybutylene terephthalate, poly-1,4-cyclohexane dimethylene terephthalate, polyethylene 1,2-diphenoxyethane-4,4'-dicarboxylate, polybutylene terephthalate), and polymethyl methacrylate. Preferable are polycarbonate, polyethylene terephthalate, and acrylic resins. The polymer material according to the present invention may be used as a transparent support, and the transmittance of the transparent support in such a case is preferably 80% or more, more preferably 86% or more.

Hereinafter, the packaging material containing the ultraviolet absorbent according to the present invention will be described. The packaging material containing the ultraviolet absorbent according to the present invention may be a packaging material of any kind of polymer, as long as it contains the compound represented by any one of formulae (2) to (5). Examples thereof include the thermoplastic resins described in JP-A-8-208765; the polyesters described in JP-A-10-168292 and JP-A-2004-285189; and the heat-shrinkable polyesters described in JP-A-2001-323082. It may be, for example, the paper coated with a resin containing an ultraviolet absorbent described in JP-A-2006-240734.

The packaging material containing the ultraviolet absorbent according to the present invention may be that for packaging anything such as food, beverage, medicine, cosmetics, or individual health care product. Examples thereof include the food packaging materials described in JP-A-11-34261 and JP-A-2003-237825; the colored liquid packaging materials described in JP-A-8-80928; the liquid preparation-packaging materials described in JP-A-2004-51174; the medicine container packaging materials described in JP-A-8-301363 and JP-A-11-276550; the medical sterilization packaging materials described in JP-A-2006-271781; the photographic photosensitive material packaging materials described in JP-A-7-287353; the photograph film packaging materials described in JP-A-2000-56433; the UV-hardening ink packaging materials described in JP-A-2005-178832; the shrink labels described in JP-A-2003-200966 and JP-A-2006-323339; and the like.

The packaging material containing the ultraviolet absorbent according to the present invention may be the transparent packaging material described, for example, in JP-A-2004-51174 or the light-shielding packaging material described, for example, in JP-A-2006-224317.

The packaging material containing the ultraviolet absorbent according to the present invention may have ultraviolet light-shielding property as well as other properties, as described, for example, in JP-A-2001-26081 and JP-A-2005-305745. Examples thereof include the packaging materials having gas-barrier property described, for example, in JP-A-2002-160321; those containing an oxygen indicator as described, for example, in JP-A-2005-156220; those containing both an ultraviolet absorbent and a fluorescent brightener described, for example, in JP-A-2005-146278; and the like.

The packaging material containing the ultraviolet absorbent according to the present invention may be prepared by any method. Examples of the method include the method of forming an ink layer described, for example, in JP-A-2006-130807; the method of melt-extruding and laminating a resin containing an ultraviolet absorbent described, for example, in JP-A-2001-323082 and JP-A-2005-305745; the method of coating on a base film described, for example, in JP-A-9-142539; the method of dispersing an ultraviolet absorbent in an adhesive described, for example, in JP-A-9-157626; and the like.

Hereinafter, the container containing the ultraviolet absorbent according to the present invention will be described. The container containing the ultraviolet absorbent according to the present invention may be a container of any kind of polymer, as long as it contains the compound represented by any one of formulae (2) to (5). Examples thereof include the thermoplastic resin containers described in JP-A-8-324572; the polyester containers described in JP-A-2001-48153, JP-A-2005-105004, and JP-A-2006-1568; the polyethylene naphthalate containers described in JP-A-2000-238857; and the like.

The container containing the ultraviolet absorbent according to the present invention is used as containers in various applications including food, beverage, medicine, cosmetics, individual health care product, shampoo and the like. Examples thereof include the liquid fuel-storing containers described in JP-A-5-139434; the golf ball containers described in JP-A-7-289665; the food containers described in JP-A-9-295664 and JP-A-2003-237825; the liquor containers described in JP-A-9-58687; the medicine-filling containers described in JP-A-8-155007; the beverage containers described in JP-A-8-324572 and JP-A-2006-298456; the oily food containers described in JP-A-9-86570; the analytical reagent solution containers described in JP-A-9-113494; the instant noodle containers described in JP-A-9-239910; the light-resistant cosmetic preparation containers described in JP-A-11-180474, JP-A-2002-68322, and JP-A-2005-278678; the medicine containers described in JP-A-11-276550; the high-purity chemical solution containers described in JP-A-11-290420; the liquid agent containers described in JP-A-2001-106218; the UV-hardening ink containers described in JP-A-2005-178832; the plastic ampoules described in WO 04/93775 pamphlet; and the like.

The container containing the ultraviolet absorbent according to the present invention may have ultraviolet-shielding property as well as other properties, as described, for example, in JP-A-5-305975 and JP-A-7-40954. Examples of such containers include the antimicrobial containers described in JP-A-10-237312; the flexuous containers described in JP-A-2000-152974; the dispenser containers described in JP-A-2002-264979; the biodegradable containers described in, for example, JP-A-2005-255736; and the like.

The container containing the ultraviolet absorbent according to the present invention may be prepared by any method. Examples of the method include the two-layer stretching blow-molding method described in JP-A-2002-370723; the multilayer coextrusion blow-molding method described in JP-A-2001-88815; the method of forming an ultraviolet-absorbing layer on the external surface of an container described in JP-A-9-241407; the methods of using a shrinkable film described in JP-A-8-91385, JP-A-9-48935, JP-T-11-514387, JP-A-2000-66603, JP-A-2001-323082, JP-A-2005-105032, and WO 99/29490 pamphlet; the method of using a supercritical fluid described in JP-A-11-255925; and the like.

Hereinafter, the paint and the coated film containing the ultraviolet absorbent according to the present invention will be described. The paint containing the ultraviolet absorbent according to the present invention may be a paint of any composition, as long as it contains the compound represented by any one of formulae (2) to (5). Examples thereof include those of acrylic resin-base, and polyester resin-base. To these resins, a base compound, curing agent, diluent, leveling agent, cissing inhibitor or the like may be added.

For example, when an acrylic urethane resin or a silicon acrylic resin is selected as the transparent resin component, the curing agent is preferably polyisocyanate; and the diluent is preferably a hydrocarbon-based solvent such as toluene or xylene, an ester-based solvent such as isobutyl acetate, butyl acetate and amyl acetate, or an alcohol-based solvent such as isopropyl alcohol or butyl alcohol. The acrylic urethane resin is an acrylic urethane resin obtained by reaction of a methacrylate (typically, methyl methacrylate), hydroxyethyl methacrylate copolymer and a polyisocyanate. In such a case, the polyisocyanate is, for example, tolylene diisocyanate, diphenylmethane diisocyanate, polymethylene polyphenylene polyisocyanate, tolidine diisocyanate, naphthalene diisocyanate, hexamethylene diisocyanate, isophorone diisocyanate, xylylene diisocyanate, dicyclohexylmethane diisocyanate, hexamethylene diisocyanate or the like. Examples of other transparent resin components include polymethyl methacrylate, polymethyl methacrylate/styrene copolymer, and the like. In addition to these components, a leveling agent such as an acrylic or silicone resin, a cissing inhibitor such as a silicone-based or acrylic inhibitor, and others may be added as needed.

The paint containing the ultraviolet absorbent according to the present invention may be used in any application. Examples thereof include the ultraviolet-shielding paints described in JP-A-7-26177, JP-A-9-169950, JP-A-9-221631, and JP-A-2002-80788; the ultraviolet-infrared-shielding paints described in JP-A-10-88039; the electromagnetic wave-shielding paints described in JP-A-2001-55541; the clear paints described in JP-A-8-81643; the metallic paint compositions described in JP-A-2000-186234; the cation electrodeposition paints described in JP-A-7-166112; the antimicrobial and lead-free cation electrodeposition paints described in JP-A-2002-294165; the powder paints described in JP-A-2000-273362, JP-A-2001-279189, and JP-A-2002-271227; the aqueous intermediate-layer paints, aqueous metallic paints, and aqueous clear paints described in JP-A-2001-9357; the topcoat paints for automobile, construction, and civil work described in JP-A-2001-316630; the hardening paints described in JP-A-2002-356655; the coat-film forming compositions for use on plastic materials such as automobile bumper described in JP-A-2004-937; the paints for a metal plate described in JP-A-2004-2700; the hardening gradient coat films described in JP-A-2004-169182; the coating materials for an electric wire described in JP-A-2004-107700; the paints for automobile repair described in JP-A-6-49368; the anionic electrodeposition paints described in JP-A-2002-38084 and JP-A-2005-307161; the paints for an automobile described in JP-A-5-78606, JP-A-5-185031, JP-A-10-140089, JP-T-2000-509082, JP-T-2004-520284, and WO 2006/097201 pamphlet; the paints for a coated steel plate described in JP-A-6-1945; the paints for a stainless steel described in JP-A-6-313148; the lamp moth-repellent paints described in JP-A-7-3189; the UV-hardening paints described in JP-A-7-82454; the antimicrobial paints described in JP-A-7-118576; the eyestrain protection paints described in JP-A-2004-217727; the anti-fog paints described in JP-A-2005-314495; the ultra-weather-resistance paints described in JP-A-10-298493; the gradient paints described in JP-A-9-241534; the photocatalyst paints described in JP-A-2002-235028; the strippable paints described in JP-A-2000-345109; the concrete separation paints described in JP-A-6-346022; the anti-corrosion paints described in JP-A-2002-167545; the protective paints described in JP-A-8-324576; the water-repellent protective paints described in JP-A-9-12924; the anti-plate glass scattering paints described in JP-A-9-157581; the alkali-soluble protective paints described in JP-A-9-59539; the aqueous temporary protective paint compositions described in JP-A-2001-181558; the flooring paints described in JP-A-10-183057; the emulsion paints described in JP-A-2001-115080; the two-liquid aqueous paints described in JP-A-

2001-262056; the one-liquid paints described in JP-A-9-263729; the UV-hardening paints described in JP-A-2001-288410; the electron beam-hardening paint compositions described in JP-A-2002-69331; the thermosetting paint compositions described in JP-A-2002-80781; the aqueous paints for baking lacquer described in JP-T-2003-525325; the powder paints and the slurry paints described in JP-A-2004-162021; the repair paints described in JP-A-2006-233010; the powder-paint aqueous dispersions described in JP-T-11-514689; the paints for a plastic article described in JP-A-2001-59068 and JP-A-2006-160847; the electron beam-hardening paints described in JP-A-2002-69331; and the like.

The paint containing the ultraviolet absorbent according to the present invention generally contains a paint (containing a transparent resin component as the principal component) and an ultraviolet absorbent. The paint contains the ultraviolet absorbent preferably in an amount of 0 to 20 mass % with respect to the resin. The thickness of the film coated is preferably 2 to 1,000 μm, more preferably 5 to 200 μm. The method of coating the paint is arbitrary, and examples of the method include a spray method, a dipping method, a roller coating method, a flow coater method, a blow coating method, and the like. The dry after coating is preferably carried out at a temperature of approximately room temperature to 120° C. for 10 to 90 minutes, although the condition may vary according to the paint composition.

The coated film containing the ultraviolet absorbent according to the present invention is a coated film formed by using the paint containing the ultraviolet absorbent according to the present invention that contains the ultraviolet absorbent containing the compound represented by any one of formulae (2) to (5).

Hereinafter, the ink containing the ultraviolet absorbent according to the present invention will be described. The ink containing the ultraviolet absorbent according to the present invention may be any ink in any form, as long as it contains the compound represented by any one of formulae (2) to (5). For example, it may be dye ink, pigment ink, aqueous ink, solvent ink, or the like. It may be used in any application. Examples of the applications include the screen printing ink described in JP-A-8-3502; the flexographic printing ink described in JP-T-2006-521941; the gravure printing ink described in JP-T-2005-533915; the lithographic offset printing ink described in JP-T-11-504954; the letterpress printing ink described in JP-T-2005-533915; the UV ink described in JP-A-5-254277; the EB ink described in JP-A-2006-30596; and the like. Other examples thereof include the inkjet inks described in JP-A-11-199808, WO 99/67337 pamphlet, JP-A-2005-325150, JP-A-2005-350559, JP-A-2006-8811, and JP-T-2006-514130; the photochromic ink described in JP-A-2006-257165; the thermal transfer ink described in JP-A-8-108650; the masking ink described in JP-A-2005-23111; the fluorescence ink described in JP-A-2004-75888; the security ink described in JP-A-7-164729; the DNA ink described in JP-A-2006-22300; and the like.

Any product obtained by using the ink containing the ultraviolet absorbent according to the present invention is also included in the present invention. Examples thereof include the print described in JP-A-2006-70190, and laminated films obtained by laminating the print, and the packaging materials and containers prepared by using the laminated film; the ink-receiving layer described in JP-A-2002-127596; and the like.

Hereinafter, the fiber containing the ultraviolet absorbent according to the present invention will be described. The fiber containing the ultraviolet absorbent according to the present invention may be a fiber of any kind of polymer, as long as it contains the compound represented by any one of formulae (2) to (5). Examples thereof include the polyester fibers described in JP-A-5-117508, JP-A-7-119036, JP-A-7-196631, JP-A-8-188921, JP-A-10-237760, JP-A-2000-54287, JP-A-2006-299428, and JP-A-2006-299438; and the like.

The fiber containing the ultraviolet absorbent according to the present invention may be prepared by any method. Examples of the method include the method, as described in JP-A-6-228818, of processing a polymer previously containing the compound represented by any one of formulae (2) to (5) into fiber, and the methods, as described, for example, in JP-A-5-9870, JP-A-8-188921, and JP-A-10-1587, of processing a material processed in a fiber form with a solution containing the compound represented by any one of formulae (2) to (5). As described in JP-A-2002-212884 and JP-A-2006-16710, the fiber may be prepared by using a supercritical fluid.

The fiber containing the ultraviolet absorbent according to the present invention can be used in various applications. Examples thereof include the clothing described in JP-A-5-148703; the backing described in JP-A-2004-285516; the underwear described in JP-A-2004-285517; the blanket described in JP-A-2003-339503; the hosiery described in JP-A-2004-11062; the synthetic leather described in JP-A-11-302982; the moth-repellent mesh sheet described in JP-A-7-289097; the mesh sheet for construction described in JP-A-10-1868; the carpet described in JP-A-5-256464; the moisture-permeable water-repellent sheet described in JP-A-5-193037; the nonwoven fabric described in JP-A-6-114991; the ultrafine fiber described in JP-A-11-247028; the fibrous sheet described in JP-A-2000-144583; the refreshing clothing described in JP-A-5-148703; the moisture-permeable water-repellent sheet described in JP-A-5-193037; the flame-resistant synthetic suede cloth structure described in JP-A-7-18584; the resin tarpaulin described in JP-A-8-41785; the filming agent, external wall material, and agricultural greenhouse described in JP-A-8-193136; the net and mesh for construction described in JP-A-8-269850; the filter substrate described in JP-A-8-284063; the stainproof filming agent described in JP-A-9-57889; the mesh fabric and land net described in JP-A-9-137335; the underwater net described in JP-A-10-165045; the ultrafine fibers described in JP-A-11-247027 and 11-247028; the textile fiber described in JP-A-7-310283 and JP-T-2003-528974; the air-bag base cloth described in JP-A-2001-30861; the ultraviolet-absorbing fiber products described in JP-A-7-324283, JP-A-8-20579, and JP-A-2003-147617; and the like.

Hereinafter, the construction material containing the ultraviolet absorbent according to the present invention will be described. The construction material containing the ultraviolet absorbent according to the present invention may be a construction material of any kind of polymer, as long as it contains the compound represented by any one of formulae (2) to (5). Examples thereof include the polyester-based material described in JP-A-2002-161158; the polycarbonate-based material described in JP-A-2003-160724; and the like.

The construction material containing the ultraviolet absorbent according to the present invention may be prepared by any method. Examples of the method include the method, as described in JP-A-8-269850, of forming a material containing the compound represented by any one of formulae (2) to (5) into a desired shape; the methods, as described, for example, in JP-A-10-205056, of forming a laminate of a material containing the compound represented by any one of formulae (2) to (5); the methods, as described, for example, in JP-A-8-151457, of forming a coated layer containing the compound represented by any one of formulae (2) to (5); and the methods, as described, for example, in JP-A-2001-172531, of forming it by coating a paint containing the compound represented by any one of formulae (2) to (5).

The construction material containing the ultraviolet absorbent according to the present invention can be used in various applications. Examples thereof include the external construction materials described in JP-A-7-3955, JP-A-8-151457, and JP-A-2006-266042; the wood structure for construction described in JP-A-8-197511; the roofing material for construction described in JP-A-9-183159; the antimicrobial construction material described in JP-A-11-236734; the base construction material described in JP-A-10-205056; the antifouling construction material described in JP-A-11-300880; the flame-resistant material described in JP-A-2001-9811; the ceramic construction material described in JP-A-2001-172531; the decorative construction material described in JP-A-2003-328523; the paints for construction described in JP-A-2002-226764; the facing materials described in JP-A-10-6451, JP-A-10-16152, and JP-A-2006-306020; the construction net described in JP-A-8-269850; the moisture-permeable water-repellent sheet for construction described in JP-A-9-277414; the mesh sheet for construction described in JP-A-10-1868; the construction film described in JP-A-7-269016; the decorative film described in JP-A-2003-211538; the coating materials for construction described in JP-A-9-239921, JP-A-9-254345, and JP-A-10-44352; the adhesive composition for construction described in JP-A-8-73825; the civil work construction structure described in JP-A-8-207218; the pathway coating material described in JP-A-2003-82608; the sheet-shaped photocuring resin described in JP-A-2001-139700; the wood-protecting paint described in JP-A-5-253559; the push-switch cover described in JP-A-2005-2941780; the bond-sheeting agent described in JP-A-9-183159; the base construction material described in JP-A-10-44352; the wall paper described in JP-A-2000-226778; the decorative polyester film described in JP-A-2003-211538; the decorative polyester film for molding described in JP-A-2003-211606; the flooring material described in JP-A-2004-3191; and the like.

Hereinafter, the recording medium containing the ultraviolet absorbent according to the present invention will be described. The recording medium containing the ultraviolet absorbent according to the present invention may be any medium, as long as it contains the compound represented by any one of formulae (2) to (5). Examples thereof include the inkjet recording media described in JP-A-9-309260, JP-A-2002-178625, JP-A-2002-212237, JP-A-2003-266926, JP-A-2003-266927, and JP-A-2004-181813; the image-receiving medium for thermal transfer ink described in JP-A-8-108650; the image-receiving sheet for sublimation transfer described in JP-A-10-203033; the image-recording medium described in JP-A-2001-249430; the heat-sensitive recording medium described in JP-A-8-258415; the reversible heat-sensitive recording media described in JP-A-9-95055, JP-A-2003-145949, and JP-A-2006-167996; the information-photorecording medium described in JP-A-2002-367227; and the like.

Hereinafter, the image display device containing the ultraviolet absorbent according to the present invention will be described. The image display device containing the ultraviolet absorbent according to the present invention may be any device, as long as it contains the compound represented by any one of formulae (2) to (5). Examples thereof include the image display device employing an electrochromic element described in JP-A-2006-301268; the image display device of so-called electronic paper described in JP-A-2006-293155; the plasma display described in JP-A-9-306344; the image display device employing an organic EL element described in JP-A-2000-223271; and the like. The ultraviolet absorbent according to the present invention may be contained, for example, in the ultraviolet-absorbing layer formed in the laminated structure described in JP-A-2000-223271 or in a suitable part such as the circularly polarizing plate described, for example, in JP-A-2005-189645.

Hereinafter, the solar cell cover containing the ultraviolet absorbent according to the present invention will be described. The solar cell according to the present invention may be any kind of solar cell such as crystalline silicon solar cell, amorphous silicon solar cell, or dye-sensitized solar cell. As described in JP-A-2000-174296, a cover material has been used as a part for providing a crystalline silicon solar cell or an amorphous silicon solar cell with antifouling property, impact resistance, and durability. As described in JP-A-2006-282970, dye-sensitized solar batteries, which employ a metal oxide-based semiconductor that is activated by excitation of light (in particular, ultraviolet light) as its electrode material, have a problem of the photosensitizer colorant adsorbed being decomposed and thus the photovoltaic efficiency gradually declining, and for that reason, installation of an additional ultraviolet-absorbing layer was proposed.

The solar cell cover containing the ultraviolet absorbent according to the present invention may be a cover of any kind of polymer. Examples of the polymer include the polyester described in JP-A-2006-310461; the acrylic resin described in JP-A-2004-227843; and the like.

The solar cell cover containing the ultraviolet absorbent according to the present invention may be prepared by any method. For example, the ultraviolet-absorbing layer described in JP-A-11-40833 may be formed; the layers respectively containing the ultraviolet absorbent may be laminated, as described in JP-A-2005-129926; it may be contained in the filler layer resin, as described in JP-A-2000-91611; or a film may be formed, together with the ultraviolet absorbent-containing polymer described in JP-A-2005-346999.

The solar cell cover containing the ultraviolet absorbent according to the present invention may be in any form. Examples thereof include the film and sheet described in JP-A-2000-91610 and JP-A-11-261085; the laminate film described, for example, in JP-A-11-40833; the cover glass structure described in JP-A-11-214736; and the like. The ultraviolet absorbent may be contained in the sealer described in JP-A-2001-261904.

A glass-coating film and glass using the same containing the compound represented by any one of formulae (2) to (5) will be described. The glass and the glass-coating film may be any one in any form, so long as they contain the compound represented by any one of formulae (2) to (5). Further, they may be used for any purposes. Examples thereof include a heat ray-blocking (barrier) glass described in JP-A-5-58670 and JP-A-9-52738; a window glass described in JP-A-7-48145; a colored glass described in JP-A-8-157232, JP-A-10-45425 and JP-A-11-217234; an ultraviolet sharp-cut glass for high intensity light sources such as mercury lamp and metal halide lamp described in JP-A-8-59289; a frit glass described in JP-A-5-43266; an ultraviolet-blocking (barrier) glass for vehicles described in JP-A-5-163174; a colored heat ray-absorbing glass described in JP-A-5-270855; a fluorescent brightening agent-containing ultraviolet-absorbing insulation glass described in JP-A-6-316443; an ultraviolet and heat ray-blocking (barrier) glass for automobiles described in JP-A-7-237936; a cladding stained glass described in JP-A-7-267682; a water repellent ultraviolet and infrared ray-blocking (barrier) glass described in JP-A-7-291667; a glass for head up display of vehicles described in JP-A-7-257227; a dimming heat barrier multilayer window described in JP-A-7-232938; an ultraviolet and infrared rays cut glass described in JP-A-5-78147, JP-A-5-61835 and JP-A-8-217486; an ultraviolet ray cut glass described in JP-A-6-127974 and JP-A-7-53241; an ultraviolet and infrared rays-absorbing window glass described in JP-A-8-165146; an ultraviolet cut-off antifouling window film described in JP-A-10-17336; a light transmission panel for plantation house described in JP-A-9-67148; an ultraviolet and infrared rays-absorbing and low transmission glass described in JP-A-10-114540; a low reflectance and low permeability glass described in JP-A-11-302037; an edge-light apparatus described in JP-A-2000-16171; a rough surface-formed plate glass described in JP-A-2000-44286; a laminated display glass described in JP-A-2000-103655; a conductive coating glass described in JP-A-2000-133987; an anti-glare glass described in JP-A-2000-191346; an ultraviolet and infrared rays-absorbing and middle transmission glass described in JP-A-2000-7371; a privacy-protected window glass for vehicles described in JP-A-2000-143288; an anti-fogged glass for vehicles described in JP-A-2000-239045; a glass for paving materials described in JP-A-2001-287977; a drain anti-adhesion and heat ray-blocking glass plate described in JP-A-2002-127310; an ultraviolet and infrared rays-absorbing bronze glass described in JP-A-2003-342040; a glass described in WO 01/019748; a glass with ID identification function described in JP-A-2004-43212; a PDP optical filter described in JP-A-2005-70724; and a garret window described in JP-A-2005-105751. The glass-coating film containing the compound represented by any one of formula (2) to (5) and the glass using the film may be produced according to any method.

Other examples of applications include the illumination light source covers described in JP-A-8-102296, 2000-67629, and JP-A-2005-353554; the synthetic leathers described in JP-A-5-272076 and JP-A-2003-239181; the sport goggle described in JP-A-2006-63162; the deflection lens described in JP-A-2007-93649; the hard-coat film for various plastic products described in JP-A-2001-214121, JP-A-2001-214122, JP-A-2001-315263, JP-A-2003-206422, JP-A-2003-25478, JP-A-2004-137457, and JP-A-2005-132999; the hard-coat film for bonding on external window described in JP-A-2002-36441; the window film described in JP-A-10-250004; the high-definition antiglare hard-coat film described in JP-A-2002-36452; the antistatic hard-coat film described in JP-A-2003-39607; the permeable hard-coat film described in JP-A-2004-114355; the antiforgery recoding media described in JP-A-2002-113937; the turf purpura-preventing agent described in JP-A-2002-293706; the resin film/sheet-bonding sealant described in JP-A-2006-274179; the optical parts described in JP-A-2005-326761; the rubber-coating agent described in JP-A-2006-335855; the agricultural covering materials described in JP-A-10-34841 and JP-A-2002-114879; the color candles described in JP-T-2004-532306 and JP-T-2004-530024; the cloth-rinsing agent composition described in JP-T-2004-525273; the prism sheet described in JP-A-10-287804; the protective layer transfer sheet described in JP-A-2000-71626; the photocuring resin product described in JP-A-2001-139700; the flooring sheet described in JP-A-2001-159228; the light-blocking printing label described in JP-A-2002-189415; the fuel cup described in JP-A-2002-130591; the articles with hard-coat film described in JP-A-2002-307619; the intermediate transfer recording medium described in JP-A-2002-307845; the synthetic hair described in JP-A-2006-316395; the low-temperature heat-shrinkable films for label described in WO 99/29490 pamphlet and JP-A-2004-352847; the fishing goods described in JP-A-2000-224942; the micro beads described in JP-A-8-208976; the precoated metal plate described in JP-A-8-318592; the thin film described in JP-A-2005-504735; the heat-shrinkable film described in JP-A-2005-105032; the in-mold molding label described in JP-A-2005-37642; the projection screen described in JP-A-2005-55615; the decorative sheets described in JP-A-9-300537, JP-A-2000-25180, JP-A-2003-19776, and JP-A-2005-74735; the hot-melt adhesive described in JP-A-2001-207144; the adhesives described in JP-T-2002-543265, JP-T-2002-543266 and U.S. Pat. No. 6,225,384; the electrodeposition coat and the basecoat described in JP-A-2004-352783; the wood surface-protecting agent described in JP-A-7-268253; the light-controlling materials, light-controlling films, and light-controlling glasses described in JP-A-2003-253265, JP-A-2005-105131, JP-A-2005-300962, and Japanese Patent No. 3915339; the moth-repellent lamp described in JP-A-2005-304340; the touch panel described in JP-A-2005-44154; the sealant for bonding resin film sheet described in JP-A-2006-274197; the polycarbonate film coating material described in JP-A-2006-89697; the optical fiber tape described in JP-A-2000-231044; the solid wax described in JP-T-2002-527559; and the like.

Hereinafter, the method of evaluating the light stability of the polymer material will be described. Preferable methods of evaluating the light stability of the polymer material are described, for example, in "Methods for Improving the Photostability of Polymers" (CMC Publishing, 2000) p. 85 to 107; "Basis and Physical Properties of High Functional Coatings" (CMC Publishing, 2003), p. 314 to 359; "Durability of Polymer Materials and Composite Material Products" (CMC Publishing, 2005); "Elongation of Lifetime of Polymer Materials and Environmental Measures" (CMC Publishing, 2000); H. Zweifel Ed., "Plastics Additives Handbook, 5th Edition" (Hanser Publishers), p. 238 to 244; and Tadahiko Kutsura, "Basic Seminar 2. Science of Plastic Packaging Container" (Society of packaging Science & Technology, Japan, 2003), Chapter 8.

In addition, the light stability in each application can be evaluated by the following known evaluation methods.

The photodegradation of polymer materials can be determined by the method described in JIS-K7105:1981, JIS-K7101:1981, JIS-K7102:1981, JIS-K7219:1998, JIS-K7350-1:1995, JIS-K7350-2:1995, JIS-K7350-3:1996, JIS-K7350-4:1996 or a method referring to those.

The light stability in the packaging or container application can be determined by the method of JIS-K7105 and a method referring to that. Typical examples thereof include the light transmittance and transparency evaluation of the bottle body and the functional test of the bottle content after ultraviolet irradiation by using a xenon light source described in JP-A-2006-298456; the haze value evaluation after xenon lamp irradiation described in JP-A-2000-238857; the haze value evaluation by using a halogen lamp as the light source described in JP-A-2006-224317; the yellowing evaluation after mercury lamp irradiation by using a blue wool scale described in JP-A-2006-240734; the haze value evaluation by using Sunshine Weather Meter and the visual observation of color development described in JP-A-2005-105004 and JP-A-2006-1568; the ultraviolet light transmittance evaluation described in JP-A-7-40954, JP-A-8-151455, JP-A-10-168292, JP-A-2001-323082, and JP-A-2005-146278; the ultraviolet-blocking evaluation described in JP-A-9-48935 and 9-142539; the light transmittance evaluation described in JP-A-9-241407, JP-A-2004-243674, JP-A-2005-320408, JP-A-2005-305745, and JP-A-2005-156220; the evaluation of the viscosity of the ink in ink container described in JP-A-2005-178832; the light transmittance evaluation, the visual observation of the container sample and the color difference ΔE evaluation after sunlight irradiation described in JP-A-2005-278678; the ultraviolet light transmittance evaluation, the light transmittance evaluation, and the color difference evaluation after white fluorescent lamp irradiation described in JP-A-2004-51174; the light transmittance evaluation, the haze value evaluation, and the color tone evaluation described in JP-A-2004-285189; the yellowness index evaluation described in JP-A-2003-237825; the light-blocking evaluation and the brightness evaluation by using the color difference Formula of the L*a*b* color system described in JP-A-2003-20966; the yellowing evaluation by using the color difference ΔEa*b* of a sample after irradiation of xenon lights of different in wavelength described in JP-A-2002-68322; the ultraviolet absorbance evaluation after ultraviolet light irradiation described in JP-A-2001-26081; the film tensile elongation test after photoirradiation by using Sunshine Weather Meter described in JP-A-10-298397; the antimicrobial evaluation after photoirradiation in a xenon weather meter described in JP-A-10-237312; the evaluation of discoloration of a package content after fluorescent lamp irradiation described in JP-A-9-239910; the evaluation of oil peroxide value and color tone after fluorescent lamp irradiation of a salad oil-filled bottle described in JP-A-9-86570; the evaluation of the difference in absorbance after chemical lamp irradiation described in JP-A-8-301363; the evaluation of surface glossiness retention rate and appearance after photoirradiation by using Sunshine Weather Meter described in JP-A-8-208765; the evaluation of color difference and bending strength after photoirradiation by using Sunshine Weather-O-meter described in JP-A-7-216152; the light-blocking rate evaluation and the evaluation of the peroxide generated in kerosene described in JP-A-5-139434; and the like.

The long-term durability thereof when the polymer material is used in the coating and coat film applications can be evaluated according to the method of JIS-K5400, JIS-K5600-7-5:1999, JIS-K5600-7-6:2002, JIS-K5600-7-7:1999, JIS-K5600-7-8:1999, or JIS-K8741 or a method referring to those. Typical examples thereof include the evaluation of the color density, the color difference ΔEa*b* in the CIE L*a*b* color coordinates, and the residual brilliance after photoirradiation in an xenon light-endurance test machine and an UVCON apparatus described in JP-T-2000-509082; the absorbance evaluation after photoirradiation on a film placed on a quartz slide in an xenon arc light-endurance test machine and the evaluation of the color density and the color difference ΔEa*b* in the CIE L*a*b* color coordinates after fluorescent or UV lamp irradiation on wax described in JP-T-2004-520284; the color tone evaluation after photoirradiation in a Metalweather weather-resistance test machine described in JP-A-2006-160847; the evaluation of brilliance retention rate after photoirradiation test by using a metal HID lamp, the evaluation by using color difference ΔEa*b*, and the evaluation of glossiness after photoirradiation by a sunshine carbon arc light source described in JP-A-2005-307161; the evaluation by using color difference ΔEa*b* after photoirradiation in a Metalweather weather-resistance test machine, the brilliance retention rate evaluation, and the appearance evaluation described in JP-A-2002-69331; the brilliance retention rate evaluation after photoirradiation by using Sunshine Weather-O-Meter described in JP-A-2002-38084; the evaluation by using the color difference ΔEa*b* after photoirradiation in a QUV weather-resistance test machine and the brilliance retention rate evaluation described in JP-A-2001-59068; the brilliance retention rate evaluation after photoirradiation by using Sunshine Weather-O-Meter described in JP-A-2001-115080, JP-A-6-49368, and JP-A-2001-262056; the evaluation of post-irradiation appearance after photoirradiation on a coated plate by using Sunshine Weather-O-Meter described in JP-A-8-324576, JP-A-9-12924, JP-A-9-169950, JP-A-9-241534, and JP-A-2001-181558; the evaluation of the brilliance retention rate and the fluctuation in brightness after photoirradiation by using Sunshine Weather-O-Meter described in JP-A-2000-186234; the evaluation of the appearance of the deteriorated coated film after dew cycle WOM photoirradiation on coated film described in JP-A-10-298493; the evaluation of the ultraviolet light transmittance of coated film described in JP-A-7-26177; the evaluation of the ultraviolet-blocking rate of coated film described in JP-A-7-3189 and JP-A-9-263729; the comparative evaluation of the period until the brilliance retention rate of the coated film declines to 80% by using Sunshine Weather-O-Meter as described in JP-A-6-1945; the evaluation of rusting after photoirradiation by using a Dew-panel Light Control Weather Meter described in JP-A-6-313148; the evaluation of the strength of a concrete to the coated formwork after external exposure described in JP-A-6-346022; the evaluation by using the color difference ΔEa*b* after external photoirradiation, the lattice adhesion test, and the surface appearance evaluation described in JP-A-5-185031; the brilliance retention rate evaluation after external photoirradiation described in JP-A-5-78606; the evaluation of post-irradiation yellowing (ΔYI) by using a carbon arc light source described in JP-A-2006-63162; and the like.

The light stability when the polymer material is used in the ink application is determined by the method of JIS-K5701-1:2000, JIS-K7360-2, or ISO105-B02 or a method referring to those. Specific examples thereof include the evaluation of the color density and the measurement by the CIE L*a*b* color coordinates after photoirradiation by using an office fluorescent lamp or a discoloration tester described in JP-T-2006-514130; the electrophoretic evaluation after ultraviolet light irradiation by using an xenon arc light source described in JP-A-2006-22300; the print concentration evaluation with a xenon fade meter described in JP-A-2006-8811; the ink blurring evaluation by using a 100 W chemical lamp described in JP-A-2005-23111; the evaluation of the dye residual ratio in the image-forming range by using a weather meter described in JP-A-2005-325150; the evaluation of print chalking and discoloration by using an Eye Super UV Tester described in JP-A-2002-127596; the evaluation of print by using the color difference ΔEa*b* in the CIE L*a*b* color coordinates after photoirradiation by a xenon fade meter described in JP-A-11-199808 and JP-A-8-108650; the reflectance evaluation after photoirradiation by using a carbon arc light source described in JP-A-7-164729; and the like.

The light stability of the solar cell module can be determined according to the method of JIS-C8917:1998 or JIS-C8938:1995 or a method referring to those. Specific examples thereof include the I-V-measuring photovoltaic efficiency evaluation after photoirradiation by a xenon lamp light source having a sunlight-simulating compensation filter described in JP-A-2006-282970; and the evaluation of discoloration gray scale degree, color, and apparent adhesiveness after photoirradiation by using Sunshine Weather Meter or a fade mater described in JP-A-11-261085 and JP-A-2000-144583.

The light stability of fibers and fiber products can be evaluated according to the method of JIS-L1096:1999, JIS-A5905:2003, JIS-L0842, JIS-K6730, JIS-K7107, DIN75.202, SAEJ1885, SN—ISO-105-B02, or AS/NZS4399 or a method referring to those. Examples thereof include the ultraviolet light transmittance evaluation described in JP-A-10-1587, JP-A-2006-299428, and JP-A-2006-299438; the blue scale discoloration evaluation after photoirradiation by using a xenon light source or a carbon arc light source described in JP-A-6-228816, JP-A-7-76580, JP-A-8-188921, JP-A-11-247028, JP-A-11-247027, JP-A-2000-144583, JP-A-2002-322360, JP-A-2003-339503, and JP-A-2004-11062; the UV-blocking rate evaluation described in JP-A-2003-147617; the ultraviolet-blocking property evaluation described in JP-A-2003-41434; the blue scale discoloration evaluation after dry cleaning and after irradiation by using a carbon arc light source described in JP-A-11-302982; the evaluation of lightness index and color difference $\Delta E^*$ according to chromaticness index after irradiation by using a Fade-O-meter described in JP-A-7-119036 and JP-A-10-251981; the tensile strength evaluation after photoirradiation by using a UV tester or Sunshine Weather Meter described in JP-A-9-57889, JP-A-9-137335, JP-A-10-1868, and JP-A-10-237760; the total transmission and strength retention evaluation described in JP-A-8-41785 and JP-A-8-193136; the ultraviolet protection factor (UPF) evaluation described in JP-T-2003-528974, JP-T-2005-517822, and JP-A-8-20579; the discoloration gray scale evaluation after irradiation by using a high-temperature fade meter described in JP-A-6-228818, JP-A-7-324283, JP-A-7-196631, and JP-A-7-18584; the appearance evaluation after external photoirradiation described in JP-A-7-289097; the evaluation of yellowness index (YI) and yellowing degree ($\Delta$YI) after ultraviolet irradiation described in JP-A-7-289665; the remission evaluation described in JP-T-2003-528974; and the like.

The light stability of the construction material can be evaluated according to the method of JIS-A1415:1999 or a method referring to that. Specific examples thereof include the surface color tone evaluation after photoirradiation by using Sunshine Weather-O-Meter described in JP-A-2006-266402; the appearance evaluation after irradiation by using a carbon arc light source, the post-irradiation appearance evaluation by using an Eye Super UV Tester, the post-irradiation absorbance evaluation, the post-irradiation chromaticity, the color difference evaluation, the evaluation by using the color difference $\Delta Ea^*b^*$ of CIE $L^*a^*b^*$ color coordinates after photoirradiation by using a metal HID lamp light source, and brilliance retention rate evaluation described in JP-A-2004-3191 and JP-A-2006-306020; the evaluation of the change in haze value after photoirradiation by using Sunshine Weather Meter and the elongation retention rate after photoirradiation by using a tensile test machine described in JP-A-10-44352, JP-A-2003-211538, JP-A-9-239921, JP-A-9-254345, and JP-A-2003-211606; the evaluation of ultraviolet transmittance after solvent dip-coating and the visual evaluation of post-irradiation appearance by using an Eye Super UV Tester described in JP-A-2002-161158; the evaluation of brilliance change after a QUV test described in JP-A-2002-226764; the brilliance retention rate evaluation after irradiation by using Sunshine Weather-O-Meter described in JP-A-2001-172531; the evaluation by using the color difference $\Delta Ea^*b^*$ after ultraviolet irradiation by using a black light blue fluorescent lamp described in JP-A-11-300880; the evaluation of post-irradiation adhesion retention rate and ultraviolet-blocking property by using a UVCON acceleration test machine described in JP-A-10-205056; the appearance evaluation, the total light transmittance evaluation, the haze change evaluation, and tensile shear adhesive strength evaluation after external exposure (JIS-A1410) described in JP-A-8-207218 and JP-A-9-183159; the evaluation of total light transmittance of the light in the entire wavelength range, the haze evaluation, and the yellowing degree evaluation after irradiation by using a xenon weather meter described in JP-A-8-151457; the evaluation of yellowing degree ($\Delta$YI) and ultraviolet absorbent residual ratio after irradiation by using Sunshine Weather-O-Meter described in JP-A-7-3955; and the like.

The light stability when the polymer material is used in the recording medium application can be evaluated according to the method of JIS-K7350 or a method referring to that. Specific examples thereof include the evaluation of the difference in base color in the printing unit after fluorescent lamp irradiation described in JP-A-2006-167996; the evaluation of image density residual rate after irradiation by using a xenon weather meter described in JP-A-10-203033 and JP-A-2004-181813; the evaluation of the change in reflection density after irradiation by using a xenon weather meter described in JP-A-2002-207845; the yellowing degree evaluation based on the $L^*a^*b^*$ evaluation system after irradiation by using a Santest CPS photodiscoloration tester described in JP-A-2003-266926; the post-irradiation discoloration evaluation by using a fade meter described in JP-A-2003-145949; the visual evaluation of post-irradiation discoloration by using a xenon fade meter described in JP-A-2002-212237; the color density retention rate evaluation after indoor sunlight irradiation and the post-irradiation color density retention rate evaluation by using a xenon weather meter described in JP-A-2002-178625; the evaluation of post-exposure C/N by using a fade meter described in JP-A-2002-367227; the fog density evaluation after fluorescent lamp irradiation described in JP-A-2001-249430; the optical reflection density evaluation and the erasability evaluation after irradiation by using a fluorescent lamp described in JP-A-9-95055; the evaluation of post-irradiation color difference $\Delta E^*$ by using an Atlas fade meter described in JP-A-9-309260; the visual evaluation of post-irradiation discoloration by using a carbon arc fade meter described in JP-A-8-258415; the evaluation of the retention rate of organic EL element color-changing property described in JP-A-2000-223271; the measurement and evaluation of organic EL display brightness after photoirradiation by a xenon discoloration tester described in JP-A-2005-189645; and the like.

Other evaluation methods include those of JIS-K7103 and ISO/DIS9050 or a method referring to those. Specific examples thereof include the appearance evaluation after irradiation of a polycarbonate coating film by a UV tester described in JP-A-2006-89697; the blue scale evaluation after irradiation of a synthetic hair with ultraviolet light described in JP-A-2006-316395; the evaluation of water contact angle on a test cloth after irradiation by using an accelerated weather-resistance test machine described in JP-A-2006-335855; the evaluation of a visual image projected on a projection screen after irradiation by using a weather-resistance test machine described in JP-A-2005-55615; the evaluation of the deterioration of sample surface and visual evaluation of appearance after irradiation by using a Sunshine Weather Meter or a metal weather meter described in JP-A-2005-74735; the visual evaluation of appearance after photoirradiation by using a metal lamp reflector described in JP-A-2005-326761; the evaluation of the light transmittance of bottle label described in JP-A-2002-189415 and JP-A-2004-352847; the evaluation of polypropylene deterioration after irradiation by using a xenon weather meter under humid condition described in JP-A-2003-19776; the evaluation of the deterioration of a hard-coat film by using Sunshine Weather-O-Meter, and the deterioration evaluation, the hydrophilicity evaluation and the abrasion resistance evaluation of the base material described in JP-A-2002-36441 and JP-A-2003-25478; the evaluation of the gray scale color difference of synthetic leather after irradiation by using a xenon lamp light described in JP-A-2003-239181; the evaluation of liquid crystal device characteristics after irradiation by using a mercury lamp described in JP-A-2003-253265; the post-irradiation adhesiveness evaluation by using Sunshine Weather-O-Meter described in JP-A-2002-307619; the evaluation of the degree of turf purpura described in JP-A-2002-293706; the evaluation of ultraviolet light transmittance and tensile strength after irradiation by using a xenon arc light source described in JP-A-2002-114879; the concrete adhesion velocity evaluation described in JP-A-2001-139700; the appearance evaluation and the coated-film adhesiveness evaluation after irradiation by using Sunshine Weather-O-Meter described in JP-A-2001-315263; the evaluation of post-irradiation yellowing degree and adhesiveness by using a carbon arc light source described in JP-A-2001-214121 and JP-A-2001-214122; the adhesiveness evaluation by using a ultraviolet fade meter described in JP-A-2001-207144; the evaluation of insect-repellency when illumination is turned on described in JP-A-2000-67629; the evaluation of the laminated glass yellowing degree (ΔYI) by using an Eye Super UV Tester described in JP-A-10-194796; the evaluation of the surface appearance and brilliance retention rate after QUV irradiation and humidity-resistance tests described in JP-A-8-318592; the evaluation of color difference over time by using a dew panel light control weather meter described in JP-A-8-208976; the evaluation of the glossiness (DI) and the yellowness index (YI) in the wood base-coated state after irradiation by using a xenon Weather-O-meter described in JP-A-7-268253; the ultraviolet absorbance evaluation after repeated processing of UV irradiation and storage in dark described in JP-T-2002-5443265 and JP-T-2002-543266; the evaluation of dye discoloration color difference ΔE after ultraviolet irradiation described in JP-T-2004-532306; and the like.

The polymer material according to the present invention has advantageous effects that it is superior in productivity when kneaded with a polymer or dissolved in a solvent, resistant to precipitation of the ultraviolet absorbent and bleeding out during long-term use, long-wavelength ultraviolet absorption capacity, and lightfastness (ultraviolet light fastness) while keeping the absorption capacity for an extended period of time. In addition, the ultraviolet absorbent is also superior in convenience in handling, as it has a structure not irritant to the skin.

The polymer material according to the present invention, which has favorable lightfastness, can be used for polymeric molded products such as plastic, containers, coatings, coated films, fibers and construction materials. It can also be used, with its superior long-wavelength ultraviolet absorption capacity, in applications for protection of products sensitive to ultraviolet light, such as filter, packaging material, containers, coating, coated film, ink, fiber, construction material, recording medium, image display device and solar cell cover and also in applications for prevention of decomposition of photo-sensitive compounds.

The polymer material according to the present invention can also be used in the cosmetic application. The cosmetic preparation containing the polymer material according to the present invention has advantageous effects that it is resistant to precipitation or yellowing of the ultraviolet absorbent during production of the cosmetic preparation, superior in long-wavelength ultraviolet absorption capacity and also in retention of the absorption capacity for an extended period of time. The ultraviolet absorbent is also advantageous in that it has a structure not irritant to the skin.

In addition, the compound to be used in the polymer material according to the present invention has favorable effects that it has favorable long-wavelength ultraviolet absorption capacity, is resistant to precipitation or bleeding out when used in the polymer material and effective in improving lightfastness, as described above. Further, the compound can protect UV-sensitive organic materials, especially human and animal skins and hairs, from the damaging action by UV irradiation and is thus favorable as a photoprotecting agent for use in cosmetic products and pharmaceutical preparations for human and animals.

EXAMPLES

The present invention will be described in more detail based on the following examples, but the invention is not intended to be limited thereby. In Examples below, Compound A is the intermediate 2 described in Journal of Chemical Crystallography, 27, 997, p. 516 that is represented by the following Formula.

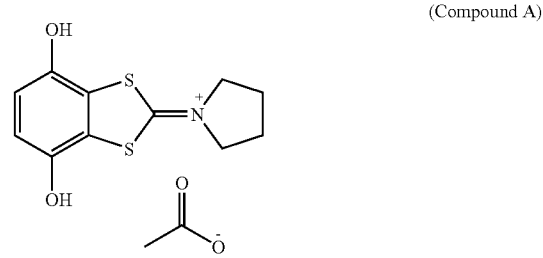

(Compound A)

Synthetic Example 1

Preparation of Exemplified Compound (S-01)

30 ml of N-methylpyrrolidone and 3.00 g (0.024 mole) of pivaloyl acetonitrile were added to 6.26 g (0.02 mole) of Compound A; the mixture was stirred at 80° C. under nitrogen flow for 4 hours, cooled and treated with ethyl acetate and dilute hydrochloric acid; and the solid precipitates generated by addition of hexane were collected by filtration (6.10 g). 3.07 g (10 mmol) of Compound B thus obtained was dissolved in 30 ml of tetrahydrofuran; 1.8 g (23 mmol) of pyridine was added thereto; and the mixture was cooled to 0° C. 3.2 g (20 mmol) of 2-ethylhexanoyl chloride was added then, and the mixture was returned back to room temperature and heated to 60° C. and stirred for 4 hours. The solution was treated with ethyl acetate and dilute hydrochloric acid, and subsequent chromatography on silica gel column (hexane/ethyl acetate=9/1) gave a desired product (amount: 5.3 g, yield: 47%). The maximum absorption wavelength (λmax) of the exemplified compound (S-01) was 375 nm (EtOAc), indicating that the compound had long-wavelength ultraviolet absorption capacity.

Mass spectrometric analysis, m/z: 559.8

$^1$H NMR (CDCl$_3$) δ 0.90-1.00 (m, 6H), 1.02-1.11 (m, 6H), 1.35-1.45 (m, 8H), 1.40 (s, 9H), 1.62-1.90 (m, 8H), 2.56-2.68 (m, 2H), 7.27 (s, 2H)

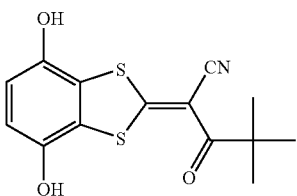

(Compound B)

Synthetic Example 2

Preparation of Exemplified Compound (S-06)

3.07 g (10 mmol) of Compound B was dissolved in 50 ml of dimethylacetamide; 5.5 g (24 mmol) of potassium carbonate and 4.6 g (24 mmol) of 2-ethylhexyl bromide were added thereto; and the mixture was stirred at 80° C. for 4 hours. Treatment with ethyl acetate and dilute hydrochloric acid and recrystallization from ethyl acetate-acetonitrile solution gave a desired product (amount: 8.32 g, yield: 52%). The maximum absorption wavelength (λmax) of the exemplified compound (S-06) was 382 nm (EtOAc), indicating that the compound had long-wavelength ultraviolet absorption capacity.

Mass spectrometric analysis, m/z 532.0

$^1$H NMR (CDCl$_3$) δ 0.88-0.99 (m, 12H), 1.28-1.39 (m, 8H), 1.42 (s, 9H), 1.43-1.56 (m, 8H), 1.71-1.80 (m, 2H), 3.90-3.99 (m, 4H), 6.80 (s, 2H)

Synthetic Example 3

Preparation of Exemplified Compound (S-18)

30 ml of N-methylpyrrolidone and 2.71 g (0.024 mole) of cyanoethyl acetate were added to 6.26 g (0.02 mole) of Compound A; the mixture was stirred at 80° C. under nitrogen flow for 4 hours, cooled and then treated with ethyl acetate and dilute hydrochloric acid; and the solid precipitates generated by addition of hexane were collected by filtration (5.90 g). 2.9 g (10 mmol) of Compound C thus obtained was dissolved in 30 ml of tetrahydrofuran; 1.8 g (23 mmol) of pyridine was added thereto; and the mixture was cooled to 0° C. 3.1 g (20 mmol) of 2-ethylhexanoyl chloride was added then, and the mixture was turned back to room temperature and heated to 60° C. and stirred for 4 hours. The solution was treated with ethyl acetate and dilute hydrochloric acid, and subsequent chromatography on silica gel column (hexane/ethyl acetate=9/1) gave a desired product (amount: 0.7 g, yield: 18%). The maximum absorption wavelength (λmax) of the exemplified compound (S-18) was 360 nm (EtOAc), indicating that the compound had long-wavelength ultraviolet absorption capacity.

Mass spectrometric analysis, m/z 548.7

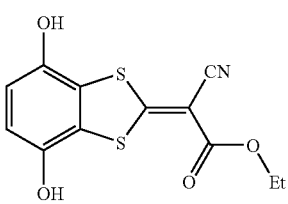

(Compound C)

Synthetic Example 4

Preparation of Exemplified Compound (S-20)

30 ml of N-methylpyrrolidone and 2.0 g (0.024 mole) of 2-cyanoacetamide were added to 6.26 g (0.02 mole) of Compound A; the mixture was stirred at 70° C. under nitrogen flow for 5 hours, cooled and treated with ethyl acetate and dilute hydrochloric acid; and the solid precipitates generated by addition of hexane were collected by filtration (4.12 g). 2.0 g (7.5 mmol) of Compound D thus obtained was dissolved in 30 ml of tetrahydrofuran; 1.8 g (23 mmol) of pyridine was added thereto; and the mixture was cooled to 0° C. 2.4 g (16 mmol) of 2-ethylhexanoyl chloride was added then, and the mixture was tuned back to room temperature and heated to 60° C. and stirred for 4 hours. The solution was treated with ethyl acetate and dilute hydrochloric acid, and subsequent chromatography on silica gel column (hexane/ethyl acetate=9/1) gave a desired product (amount: 180 g, yield: 6%). The maximum absorption wavelength (λmax) of the exemplified compound (S-20) was 357 nm (EtOAc), indicating that the compound had long-wavelength ultraviolet absorption capacity.

Mass spectrometric analysis, m/z 518.7

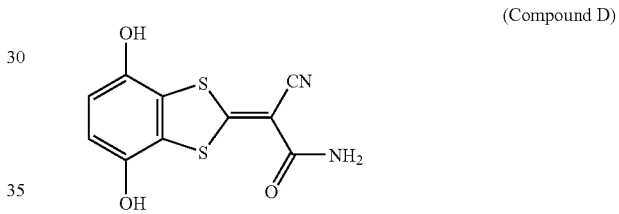

(Compound D)

Example 1

Preparation of Molded Plates

Samples 101 to 105

One (1) kg of a polymethyl methacrylate resin (PMMA) (Tg: 100 to 110° C.) and 0.1 g of the exemplified compound (S-01) were agitated in a stainless steel tumbler for 1 hour. The mixture was melted and blended by a vent extruder at 230° C. and extruded into pellets for molding by an ordinary method. The pellets were dried at 80° C. for 3 hours, and then, molded into a molded plate having a thickness of 3 mm by an injection molding machine.

Molded plates of the exemplified compounds (S-11) and (S-17) were prepared similarly, except that the exemplified compound (S-01) was replaced with the exemplified compound (S-11) or (S-17). The λmax values of the exemplified compounds (S-11) and (S-17) were respectively 377 nm and 363 nm (EtOAc), indicating that each of the compounds had long-wavelength ultraviolet absorption capacity.

Molded plates of compounds X and Y for comparison were prepared similarly, except that the exemplified compound (S-01) was replaced with the compound X or Y for comparison. The λmax values of the compounds X and Y for comparison were respectively 357 nm and 355 nm (EtOAc).

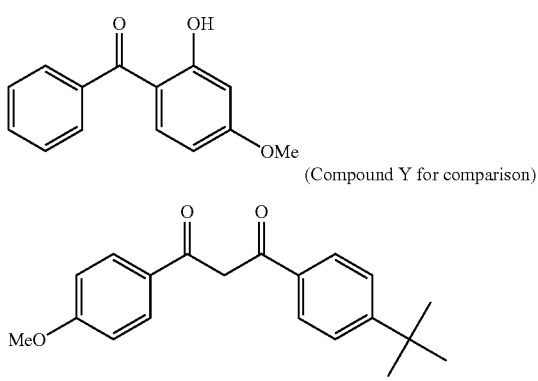

(Compound X for comparison)

(Compound Y for comparison)

(Evaluation)

Each molded plate prepared was photoirradiated by a xenon lamp with its UV filter removed at an illuminance of 150,000 lux for 100 hours, and the residual amount of the ultraviolet absorbent after irradiation was determined. The residual amount was calculated according to the following Formula:

Residual amount (%)=100×(100−Transmittance after irradiation)/(100−Transmittance before irradiation)

The transmittance is a value obtained by measurement at the λmax of the compound added. Results are summarized in Table 1.

TABLE 1

| Sample No. | Ultraviolet-absorbing compound | | Residual amount (%) | |
|---|---|---|---|---|
| 101 | Exemplified Compound (S-01) | Formula (5) | 96 | This invention |
| 102 | Exemplified Compound (S-11) | Formula (4) | 92 | This invention |
| 103 | Exemplified Compound (S-17) | Formula (3) | 89 | This invention |
| 104 | Compound X for comparison | — | 72 | Comparative example |
| 105 | Compound Y for comparison | — | 37 | Comparative example |

As obvious from the results in Table 1, the samples 104 and 105 containing the compound X or Y for comparison had a smaller residual rate of the ultraviolet absorbent after photoirradiation for 100 hours and were thus inferior in lightfastness. In contrast, while each of the samples 101 to 103 containing the compound represented by formulae (2) to (5) retained its ultraviolet absorbent in an amount of 90% or more even after photoirradiation for 100 hours, indicating its favorable lightfastness. The results show that the polymer material according to the present invention is superior in long-wavelength ultraviolet absorption capacity and also in lightfastness, as the absorption capacity is retained for an extended period of time.

Example 2

Preparation of PET Films

Samples 201 to 202

A transparent coating consisting of 100 g of DIANAL LR-1065 (trade name, manufactured by Mitsubishi Rayon, 40% methylethylketone (MEK) solution of an acrylic resin) and 0.5 g of the exemplified compound (S-02) was applied on a 100-μm polyethylene terephthalate (PET) film to be a dry film thickness of approximately 30 μM with a bar coater, and dried to give a PET film (Sample 201) having an ultraviolet-absorbing layer. The λmax value of the exemplified compound (S-02) was 392 nm (EtOAc), indicating that the compound had long-wavelength ultraviolet absorption capacity.

A PET film (Sample 202) was prepared similarly, except that the exemplified compound (S-02) was replaced with the compound Y for comparison.

(Evaluation)

A solid image in magenta color was printed on an inkjet-recording paper and dried sufficiently by using an inkjet printer (PIXUS iP1500, trade name, manufactured by Canon), and the PET film prepared above was placed and fixed thereon as an ultraviolet-absorbing layer as the outermost layer. The film was adhered to a southward window glass with its PET film facing the light and left as it was for 12 weeks for a light-resistance test.

Significant discoloration was confirmed in the Sample 202 having the ultraviolet-absorbing layer containing compound Y for comparison by visual observation. In contrast, the PET film 201 having the ultraviolet-absorbing layer containing the exemplified compound (S-02) retained a color tone almost similar to that immediately after printing. The facts mean that the polymer material according to the present invention containing the compound represented by any one of formulae (2) to (5) is also favorable as an ultraviolet-absorbing film for protection of a light-labile compound for an extended period of time.

Example 3

Preparation of Kneaded UV-Photoprotecting Agent-Containing Polymer Film

Samples 301 to 304

The exemplified compound (S-01) or (S-02) was added to 15 g polyethylene terephthalate in an amount equivalent to a transmittance at 400 nm of 1% of a 50 μm film after preparation, and the mixture was melt-kneaded at 265° C., cooled and then centrifuged, to give a UV-photoprotecting agent-containing film (sample 301 or 302). Separately, the compound Y for comparison or the exemplified compound (S-25) was also kneaded and filmed, to give a UV-photoprotecting agent-containing film (sample 303 or 304). The λmax value of the exemplified compound (S-25) was 368 nm (EtOAc), indicating that the compound had long-wavelength ultraviolet absorption capacity.

In the samples 301 and 302 containing the exemplified compound (S-01) or (S-02), the crystal melted in a short period of time without residual unmelted grains, easily giving a homogeneous and highly transparent sample.

(Evaluation)

The transmittance of the samples prepared was determined at wavelengths of 420 nm, 440 nm and 460 nm, and the color development of the samples was evaluated by visual observation. Each film prepared was photoirradiated by a xenon lamp with its UV filter removed at an illuminance of 170,000 lux for 100 hours, and the residual amount of the ultraviolet absorbent after irradiation was determined. The residual amount was calculated according to the following Formula:

Residual amount (%)=100×(100−Transmittance after irradiation)/(100−Transmittance before irradiation)

The transmittance in the light fastness test is a value determined at a wavelength of 420 nm. Results are summarized in Table 2.

TABLE 2

| Sample No. | Ultraviolet-absorbing compound | | 400 nm | 420 nm | 440 nm | 460 nm | Colored | Residual amount after light fastness test |
|---|---|---|---|---|---|---|---|---|
| 301 | Exemplified compound (S-01) | Formula (5) | 1% | 75% | 99% | 99% | ○ | 95% |
| 302 | Exemplified compound (S-02) | Formula (5) | 1% | 70% | 99% | 99% | ○ to Δ | 92% |
| 303 | Compound Y for comparison | — | 1% | 45% | 65% | 95% | X (yellow) | 40% |
| 304 | Exemplified compound (S-25) | Formula (3) | 1% | 70% | 75% | 80% | Δ to X | 90% |

○: Not colored
Δ: Slightly colored
X: Distinctly colored

As obvious from the results in Table 2, the sample 303 containing the compound Y for comparison was colored more extensively than the samples 301 and 302 containing the exemplified compound (S-01) or (S-02). The sample 304 containing the exemplified compound (S-25) having an absorption maximum shorter than that of the exemplified compounds had a lightfastness residual ratio of 90% or more but was colored, because the sample preparation amount was increased. The results show that the polymer material according to the present invention containing the compound represented by formula (5) is favorable, as it is colorless and absorbs the light in the UV-A region effectively when it is formed in a form of a film.

Example 4

Preparation of UV-Photoprotecting Agent-Containing Polymer Films

Samples 401 to 407

The exemplified compound (S-01) or (S-06) was added to 15 g of polyethylene terephthalate in an amount equivalent to absorbance of maximum absorption (Abs.) of 1 as 50 μm film, and the mixture was melt-kneaded at 265° C., cooled and then centrifuged, to give a UV-photoprotecting agent-containing film (sample 401 or 402).

Triacetate films (samples 403 to 407) were prepared, with reference to Example 2 in JP-B-49-11155, by using the exemplified compound (S-01), (S-06), (S-26) or (S-27) or the compound Z1 for comparison in an amount equivalent to the absorbance of maximum absorption (Abs.) of 1, similarly to the exemplified compound above. The λmax values of the exemplified compounds (S-26) and (S-27) were respectively 369 nm and 367 nm (EtOAc), indicating that the compounds had long-wavelength ultraviolet absorption capacity.

In samples 401 and 402 prepared respectively by using the exemplified compounds (S-01) and (S-06), the crystal melted in a short period of time without residual unmelted grains, easily giving a homogeneous and highly transparent sample.

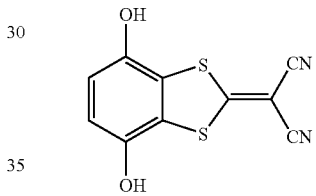

Compound Z1 for Comparison (Evaluation)

Each molded film prepared was photoirradiated by a xenon lamp with its UV filter removed at an illuminance of 170,000 lux for 50 hours, and the residual amount of the ultraviolet absorbent after irradiation was determined. The residual amount was calculated according to the following Formula:

Residual ratio (%)=100×(100−absorbance at the absorption maximum after irradiation)/(100−absorbance at the absorption maximum before irradiation)

The absorbance is a value obtained by measurement at the λmax of the compound added. Results are summarized in Table 3.

TABLE 3

| Sample No. | Ultraviolet-absorbing compound | | Residual ratio | Kind of polymer | |
|---|---|---|---|---|---|
| 401 | Exemplified compound (S-01) | Formula (5) | 90% | Polyethylene terephthalate | This invention |
| 402 | Exemplified compound (S-06) | Formula (5) | 91% | Polyethylene terephthalate | This invention |
| 403 | Exemplified compound (S-01) | Formula (5) | 50% | Triacetylcellulose | Comparative example |
| 404 | Exemplified compound (S-06) | Formula (5) | 45% | Triacetylcellulose | Comparative example |

TABLE 3-continued

| Sample No. | Ultraviolet-absorbing compound | | Residual ratio | Kind of polymer | |
|---|---|---|---|---|---|
| 405 | Compound Z1 for comparison | — | 35% | Triacetylcellulose | Comparative example |
| 406 | Exemplified compound (S-26) | Formula (3) | 45% | Triacetylcellulose | Comparative example |
| 407 | Exemplified compound (S-27) | Formula (3) | 46% | Triacetylcellulose | Comparative example |

As obvious from the results in Table 3, in the case of the triacetate film samples 403 to 407 respectively containing the exemplified compounds (S-26) and (S-27) described in JP-B-49-11155 and the compound Z1 for comparison, the ultraviolet absorbent residual rate after photoirradiation for 50 hours was lower, showing their low lightfastness. In contrast, in the case of the polyethylene terephthalate film samples 401 to 402 containing the compound represented by formula (5), 90% or more of the ultraviolet absorbent was retained even after photoirradiation for 50 hours, indicating their favorable lightfastness. The results show that the polymer material according to the present invention is superior in long-wavelength ultraviolet absorption capacity and also in lightfastness, as the absorption capacity is retained for an extended period of time.

Example 5

Preparation of UV-Photoprotecting Agent-Containing Polymer Films

Samples 501 to 506

The exemplified compound (S-01) was added to 10 g of polycarbonate (Tg 140° C. to 150° C.) in an amount equivalent to an absorption maximum absorbance (Abs.) of 1 as 5-μm film, and the mixture was dissolved in 20 ml of tetrahydrofuran and casted on a glass plate, to give a polycarbonate film (sample 501).

Similarly, the exemplified compound (S-01) was added to 10 g of a polyacrylate resin (DIANAL BR-80: trade name, manufactured by Mitsubishi Rayon) (Tg 50° C. to 90° C.); the mixture was dissolved in a mixed solvent of 10 ml of 2-butanone and 10 ml of toluene and casted on a glass plate, to give a polyacrylate film (sample 502).

Poly(vinyl chloride) films (samples 503 to 506) were prepared, with reference to Example 1 in JP-B-49-11155, by using the exemplified compound (S-01), (S-28) or (S-29) in an amount equivalent to the absorbance of maximum absorption (Abs.) of 1, similarly to the exemplified compound above. The λmax values of the exemplified compounds (S-28) and (S-29) were respectively 368 nm and 362 nm (EtOAc), indicating that the compounds had long-wavelength ultraviolet absorption capacity.

(Evaluation)

Each molded film prepared was photoirradiated by a xenon lamp with its UV filter removed at an illuminance of 190,000 lux for 50 hours, and the residual amount of the ultraviolet absorbent after irradiation was determined. The residual amount was calculated according to the following Formula:

Residual ratio (%)=100×(100−absorbance at the absorption maximum after irradiation)/(100−absorbance at the absorption maximum before irradiation)

The absorbance is a value obtained by measurement at the λmax of the compound added. Results are summarized in Table 4.

TABLE 4

| Sample No. | Ultraviolet-absorbing compound | | Residual ratio | Kind of polymer | |
|---|---|---|---|---|---|
| 501 | Exemplified compound (S-01) | Formula (5) | 93% | Polycarbonate | This invention |
| 502 | Exemplified compound (S-01) | Formula (5) | 90% | Polyacrylate | This invention |
| 503 | Exemplified compound (S-01) | Formula (5) | 58% | Poly(vinyl chloride) | Comparative example |
| 504 | Exemplified compound (S-01) | Formula (5) | 52% | Poly(vinyl chloride) | Comparative example |
| 505 | Exemplified compound (S-28) | Formula (3) | 59% | Poly(vinyl chloride) | Comparative example |
| 506 | Exemplified compound (S-29) | Formula (3) | 56% | Poly(vinyl chloride) | Comparative example |

As obvious from the results in Table 4, in the case of the poly(vinyl chloride) film samples 503 to 506 respectively containing the exemplified compounds (S-01), (S-28) or (S-29), the ultraviolet absorbent residual rate after photoirradiation for 50 hours was lower, showing their low lightfastness. In contrast, in the case of the polycarbonate film sample 501 containing the compound represented by formula (5) and the polyacrylate film sample 502 containing the compound represented by formula (5), 90% or more of the ultraviolet absorbent was retained even after photoirradiation for 50 hours, indicating their favorable lightfastness. The results show that the polymer material according to the present invention is superior in long-wavelength ultraviolet absorption capacity and also in lightfastness, as the absorption capacity is retained for an extended period of time.

Example 6

The exemplified compound (S-01) was added to 10 g of a polyacrylate resin in an amount equivalent to an absorption maximum absorbance (Abs.) of 1 as 5-μm film, and the mixture was dissolved in a mixed solvent of 10 ml of 2-butanone and 10 ml of toluene and casted on a glass plate, to give a polyacrylate film (sample 601). Plasticizer-containing polyacrylate films (602 and 603) were prepared similarly, except that 4 ml of dioctyl terephthalate and triphenyl phosphate were added to the mixed solvent, and the films were compared by lightfastness test.

(Evaluation)

The molded films prepared were photoirradiated by a xenon lamp with its UV filter removed at an illuminance of 190,000 lux, and color development of the films after irradiation for 50 hours was evaluated by visual observation. The results were grouped into the following three ranks:

○: Not colored,

Δ: Slightly colored, x: Distinctly colored.

Results are summarized in Table 5.

TABLE 5

| Sample No. | Ultraviolet-absorbing compound | Kind of polymer | Plasticizer | Coloring evaluation |
|---|---|---|---|---|
| 601 | Exemplified compound (S-01) | Polyacrylate | None | o |
| 602 | Exemplified compound (S-01) | Polyacrylate | Dioctyl terephthalate | x |
| 603 | Exemplified compound (S-01) | Polyacrylate | Triphenyl phosphate | x |

As obvious from the results in Table 5, among the resins in combination of the exemplified compound (S-01) and polyacrylate, one without any plasticizer was excellent polymer material most resistant to color development.

INDUSTRIAL APPLICABILITY

The polymer material according to the present invention can be preferably used for polymeric molded products such as plastic, containers, coatings, coated films, fibers and construction materials; and filter, packaging material, containers, coatings, coated film, ink, fiber, construction material, recording medium, image display device and solar cell cover for protection of products sensitive to ultraviolet light.

The polymer material according to the present invention can also be preferably used in the cosmetic application.

Further, the compound for used in the polymer material according to the present invention can also be preferably used as a photoprotecting agent for use in cosmetic products and pharmaceutical preparations for human and animals.

Having described our invention as related to the present embodiments, it is our intention that the invention not be limited by any of the details of the description, unless otherwise specified, but rather be construed broadly within its spirit and scope as set out in the accompanying claims.

This non-provisional application claims priority under 35 U.S.C. §119 (a) on Patent Application No. 2007-040064 filed in Japan on Feb. 20, 2007, Patent Application No. 2007-213979 filed in Japan on Aug. 20, 2007, and Patent Application No. 2007-255590 filed in Japan on Sep. 28, 2007, each of which is entirely herein incorporated by reference.

The invention claimed is:

1. A polymer material, comprising:
   at least one kind of polymer substance selected from the group consisting of acrylic acid-based polymers, polyester-based polymers, and polycarbonate-based polymers; and
   a compound represented by formula (5) contained in the polymer substance:

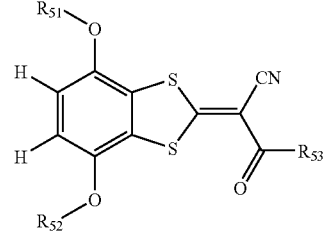

Formula (5)

wherein $R_{51}$ and $R_{52}$ each independently represent an unsubstituted alkyl group having 1 to 18 carbon atoms, or an unsubstituted alkylcarbonyl group having 2 to 18 carbon atoms; and $R_{53}$ represents an unsubstituted alkyl group having 2 to 18 carbon atoms, or an unsubstituted aryl group having 6 to 10 carbon atoms.

2. The polymer material according to claim 1, wherein a glass transition point (Tg) of the polymer substance is −80° C. or higher and 200° C. or lower.

3. The polymer material according to claim 1, wherein the polymer substance is a polyacrylate, a polycarbonate or a polyethylene terephthalate.

4. The polymer material according to claim 1,
   wherein the polymer substance is polyethylene terephthalate; and
   wherein the compound represented by formula (5) is contained in an amount of 0.1 mass % to 50 mass % with respect to 100 mass % of the polyethylene terephthalate.

5. The polymer material according to claim 4, wherein the polymer material is a polymer material prepared by melt-kneading of the polyethylene terephthalate and the ultraviolet absorbent at a temperature of 200° C. or higher.

6. The polymer material according to claim 1,
   wherein the polymer substance is polyacrylate or polycarbonate; and
   wherein the compound represented by formula (5) is contained in an amount of 0.1 mass % to 50 mass % with respect to 100 mass % of the polyacrylate or polycarbonate.

7. The polymer material according to claim 6, wherein the polymer material is a polymer material prepared by dissolving the polyacrylate and the ultraviolet absorbent in a solvent having a boiling point of 200° C. or lower to give a solution, and applying the solution on a base plate.

8. A compound represented by formula (5):

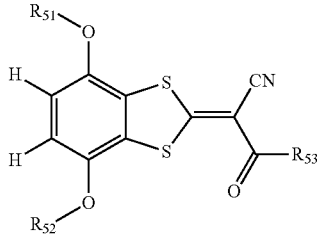

Formula (5)

wherein $R_{51}$ and $R_{52}$ each independently represent an unsubstituted alkyl group having 1 to 18 carbon atoms, or an unsubstituted alkylcarbonyl group having 2 to 18 carbon atoms; $R_{53}$ represents an unsubstituted alkyl group having 2 to 18 carbon atoms, or an unsubstituted aryl group having 6 to 10 carbon atoms.

9. An ultraviolet absorbent, comprising the compound according to claim 8.

10. A polymer material, comprising the ultraviolet absorbent according to claim 9.

11. The polymer material according to claim 1, wherein, in the compound represented by formula (5), $R_{51}$ and $R_{52}$ each independently represent a methyl group, an acetyl group, a 2-ethylhexyl group or a 2-ethylhexanoyl group.

12. The polymer material according to claim 1, wherein, in the compound represented by formula (5), $R_5$ and $R_{52}$ each independently represent a 2-ethylhexyl or a 2-ethylhexanoyl group.

13. The polymer material according to claim 1, wherein, in the compound represented by formula (5), $R_{53}$ represents an ethyl group, a propyl group, an isopropyl group, a butyl group, a tert-butyl group, a phenyl group or a naphthyl group.

14. The polymer material according to claim 1, wherein, in the compound represented by formula (5), $R_{53}$ represents a tert-butyl group or a phenyl group.

15. The compound according to claim 8, wherein $R_{51}$ and $R_{52}$ each independently represent a methyl group, an acetyl group, a 2-ethylhexyl group or a 2-ethylhexanoyl group.

16. The compound according to claim 8, wherein $R_{51}$ and $R_{52}$, each independently represent a 2-ethylhexyl or a 2-ethylhexanoyl group.

17. The compound according to claim 8, wherein $R_{53}$ represents an ethyl group, a propyl group, an iso-propyl group, a butyl group, a tert-butyl group, a phenyl group or a naphthyl group.

18. The compound according to claim 8, wherein $R_{53}$ represents a tert-butyl group or phenyl group.

* * * * *